(12) United States Patent
Austin et al.

(10) Patent No.: US 7,304,092 B1
(45) Date of Patent: Dec. 4, 2007

(54) COMPOUNDS AND METHODS FOR TREATING TUMORS, CANCER AND HYPERPROLIFERATIVE DISEASES

(75) Inventors: David J. Austin, New York, NY (US); Viet-Ahn A. Nguyen, Saffron Walden (GB); Doris Pupowicz, Marly (CH); Albert Deisseroth, San Diego, CA (US); Tao Wang, Acton, MA (US); Enrica Lerma, San Diego, CA (US)

(73) Assignee: Yale University, New Haven, CT (US)

( * ) Notice: Subject to any disclaimer, the term of this patent is extended or adjusted under 35 U.S.C. 154(b) by 226 days.

(21) Appl. No.: 10/705,483

(22) Filed: Nov. 11, 2003

Related U.S. Application Data

(60) Provisional application No. 60/425,389, filed on Nov. 12, 2002.

(51) Int. Cl.
  *A61K 31/215* (2006.01)
(52) U.S. Cl. .................. 514/529; 560/156; 514/625; 564/199
(58) Field of Classification Search ............... 564/199; 514/625, 529; 560/156
  See application file for complete search history.

(56) References Cited

OTHER PUBLICATIONS

Kathawala, FG 'Pharmaceutical secondary amides o f2-alkynic acids' CA 93:94825 (1980).*
Miller, LA 'Derivatives of propiolanilide' CA 65:38326.*

* cited by examiner

*Primary Examiner*—Amelia A. Owens
(74) *Attorney, Agent, or Firm*—Henry D. Coleman; R. Neil Sudol; William J. Sapone

(57) ABSTRACT

The present invention relates to novel compounds, pharmaceutical compositions and methods for treating tumors, cancer and hyperproliferative diseases including psoriasis, genital warts and hyperproliferative cell growth diseases, including hyperproliferative keratinocyte diseases such as hyperkeratosis, ichthyosis, keratoderma or lichen planus. These compounds are described according to the chemical structure:

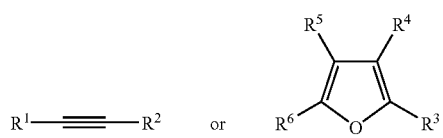

where $R^1$ is H, OH, F, Cl, Br, I, a $C_1$-$C_6$ optionally substituted alkyl or alkenyl group, an optionally substituted aryl group or a

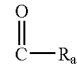

group;
$R_a$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;
$R^2$ is a

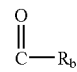

group;
$R_b$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;
$R^3$ and $R^6$ are each independently selected from H, OH, F, Cl, Br, I, a $C_1$-$C_6$ optionally substituted alkyl or alkenyl group, an optionally substituted aryl group, a carbamate, alkylene carbamate, urethane or alkylene urethane;
$R^4$ is a

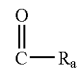

group, wherein $R_b$ is as described above; and
$R^5$ is a

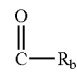

group, wherein $R_b$ is as described above,
with the proviso that at least one of $R^1$ and $R^2$ or $R^4$ and $R^5$ contains an $R_a$ or $R_b$ group which is an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;
or a stereoisomer, pharmaceutically acceptable salt, solvate, and polymorph thereof.

28 Claims, 14 Drawing Sheets

Development of planar scaffold molecules

Development of planar scaffold molecules, 2

Library of Acetylenes

FIGURE 5
1) Investigation of the scaffold left side
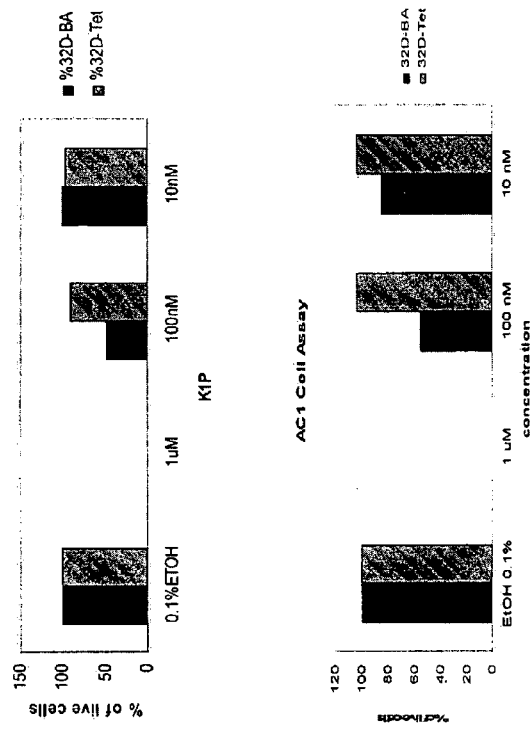
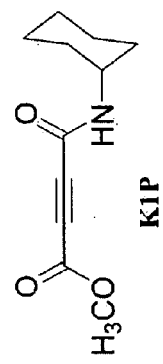
K1P
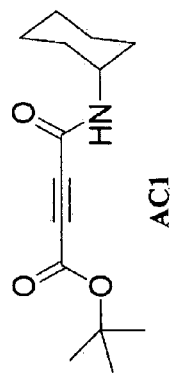
AC1
Both molecules exhibited similar activity, despite difference at the ester moiety; optimisation continued with modifications at the amide site FIGURE 7
Library of Acetylenes
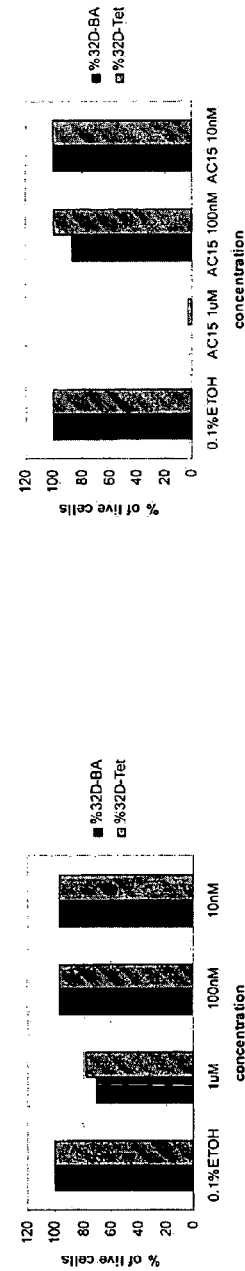
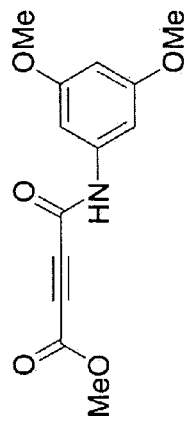
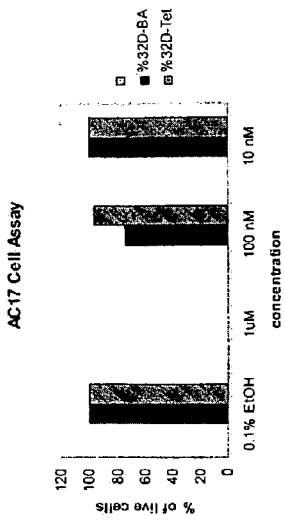
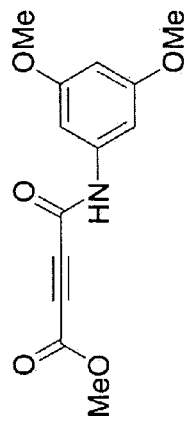
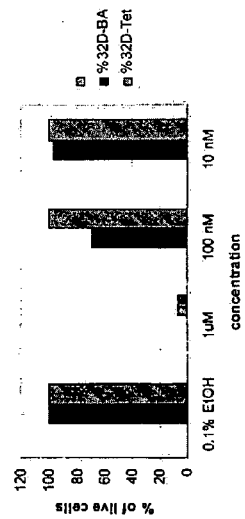

FIGURE 8
Library of Acetylenes
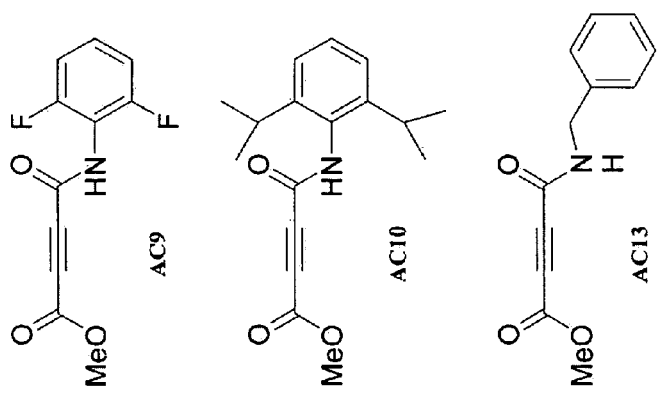
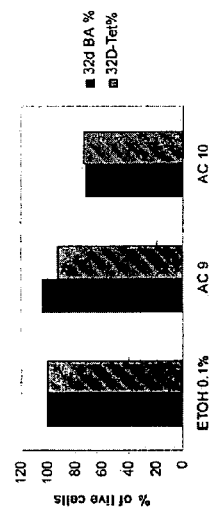
AC9
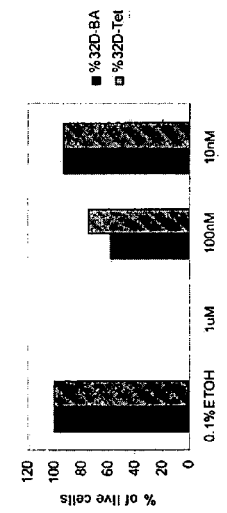
AC10
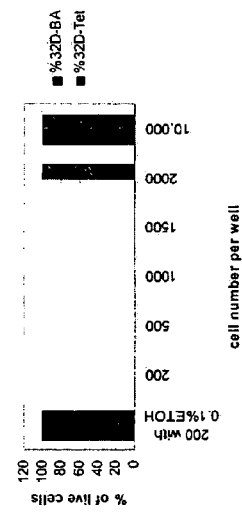
AC13
- Electron withdrawing groups on the aromatic ring are detrimental to activity
- Steric hindrance at the *o*-position has little effect on activity
- Phenyl group on the amide can be replaced by a benzyl group

FIGURE 9
Library of Acetylenes
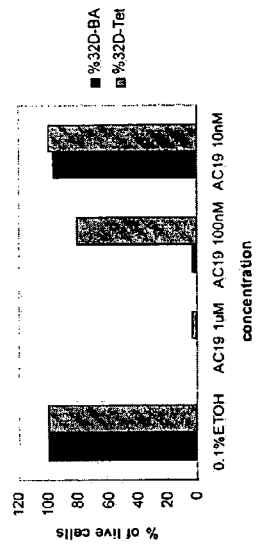
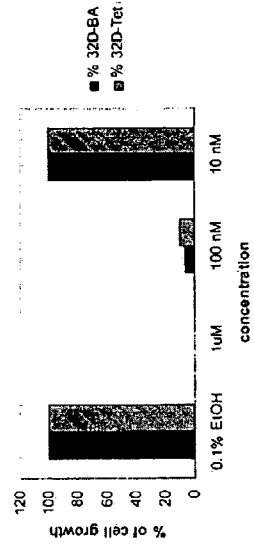
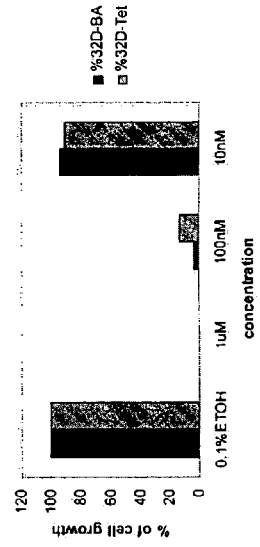
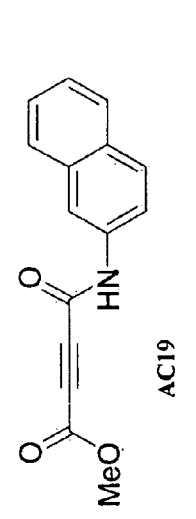
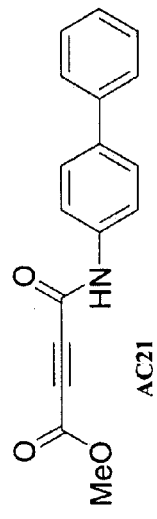
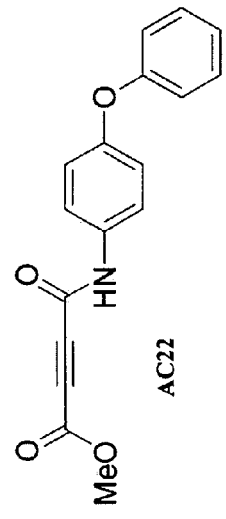
AC21 and AC22 have lost selectivity displayed by AC19 but not the activity

FIGURE 10
Some acetylenes exhibit synergism with STI-571
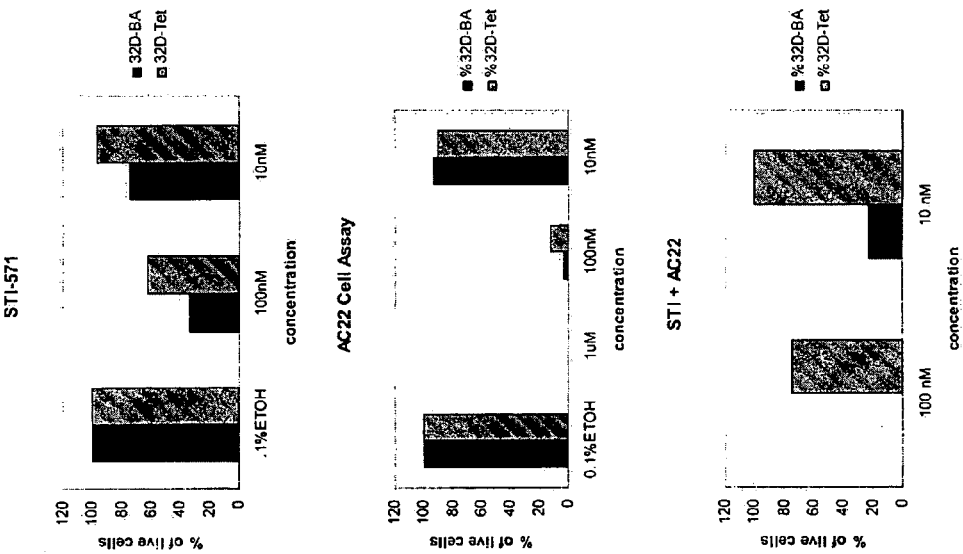
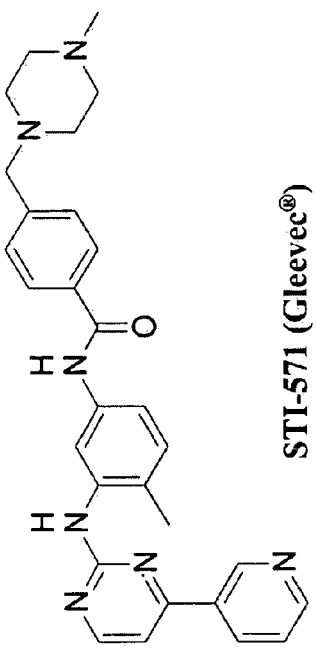
STI-571 (Gleevec®)
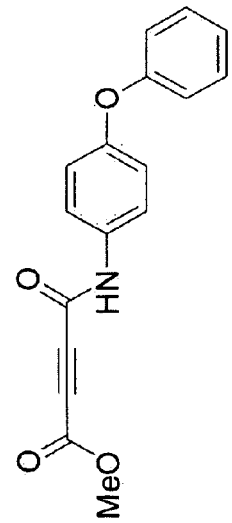
AC22
AC22 works in synergy with Gleevec®

FIGURE 11
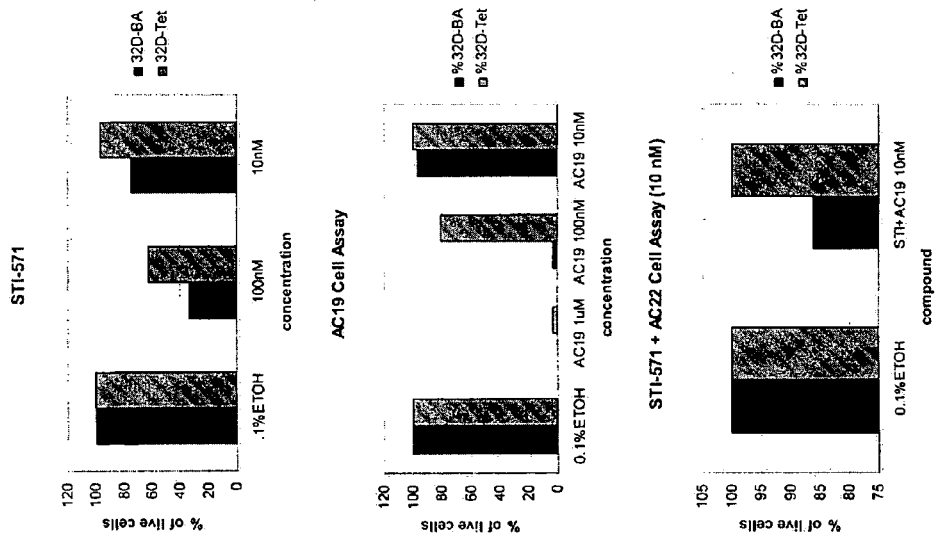
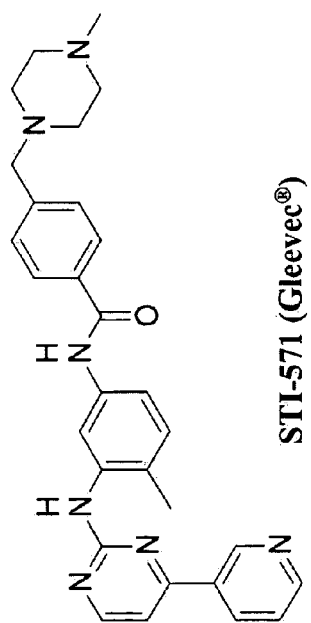
STI-571 (Gleevec®)
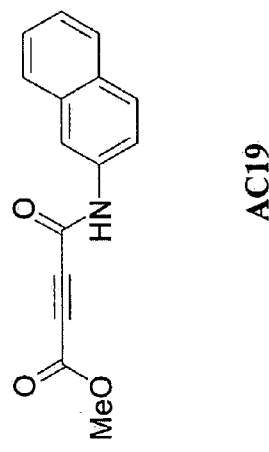
AC19

Testing of one furan from the second generation furan library

Recently, furans containing a H and a $CH_3$ were tested and proved to be active FIGURE 14
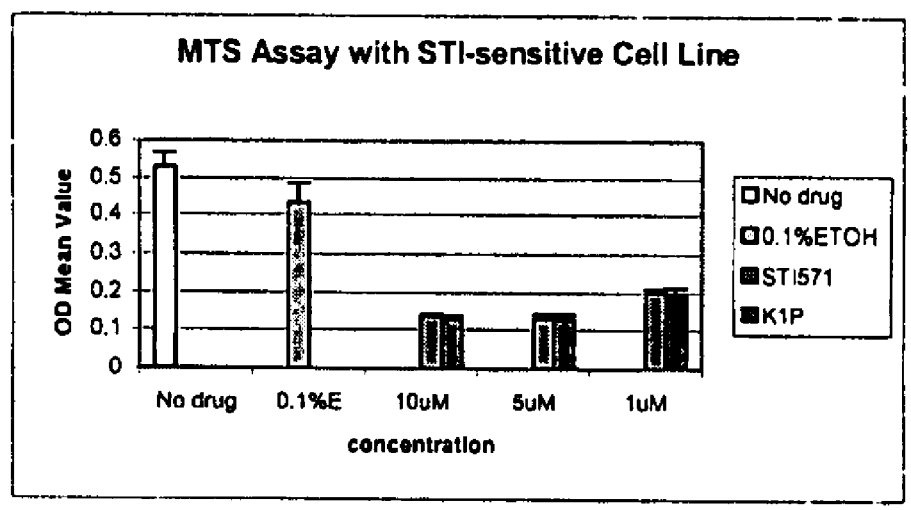
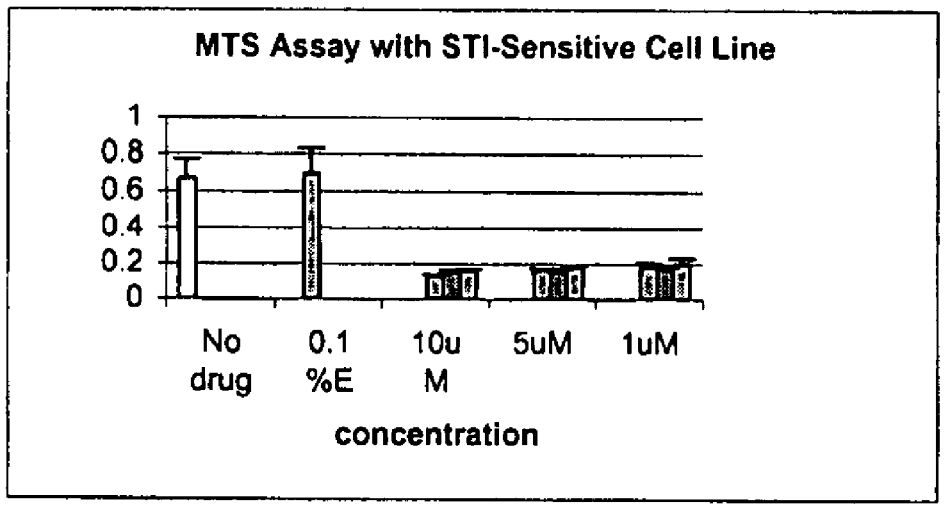

US 7,304,092 B1

COMPOUNDS AND METHODS FOR TREATING TUMORS, CANCER AND HYPERPROLIFERATIVE DISEASES

RELATED APPLICATIONS

This application claims the benefit of priority of provisional application Ser. No. 60/425,389, filed Nov. 12, 2002, entitled "Molecules for the Inhibition of Cell Proliferation, the entirety of its contents being incorporated by reference herein.

The subject matter disclosed in this application was supported, at least in part by grant number NIH/NCI P01 CA49639. As such, the government retains certain rights in the invention.

FIELD OF THE INVENTION

The present invention relates to novel compounds, pharmaceutical compositions and methods for treating tumors, cancer and hyperproliferative diseases including psoriasis, genital warts and hyperproliferative cell growth diseases, including hyperproliferative keratinocyte diseases such as hyperkeratosis, ichthyosis, keratoderma or lichen planus.

BACKGROUND OF THE INVENTION

Chronic myelogenous leukaemia (CML) is a hematological stem cell disorder that is associated with a specific chromosomal abnormality whereby the Abelson (c-abl) proto-oncogene, translocated from chromosome 9, is fused to the breakpoint cluster region (bcr) gene on chromosome 22 as shown in slide 2. The bcr-abl fusion gene codes for a tyrosine kinase that is activated constitutively and is thus able to transform cells and cause malignancy: white blood cells divide constantly leading to a blast crisis. Recently, a selective inhibitor of p210-Bcr-Abl tyrosine kinase, STI-571, was designed by Druker and co-workers. See Drucker, et al., *Nature Med.*, 2, 561-566 (1996) and Schindler, et al., *Science*, 289, 1938-1941 (2000). STI-571 (tradename: Gleevec®) is the first kinase inhibitor approved by the FDA and blocks the ATP-binding site on Abl and Bcr-Abl kinases, resulting in both inhibition of proliferation and induction of apoptosis in Bcr-Abl positive cell lines. While STI-571 leads to a complete hematological response in 96% of the patients treated for more than four weeks, patients with advanced disease often relapse, their tumor cells become resistant to the drug and these eventually grow out of control. One of the possible causes of resistance of cancerous cells to STI-571 is a mutation that replaces a single amino acid in the active site of the kinase, preventing binding of the drug to the kinase. See Gorre, et al., *Science*, 293, 876-880 (2001).

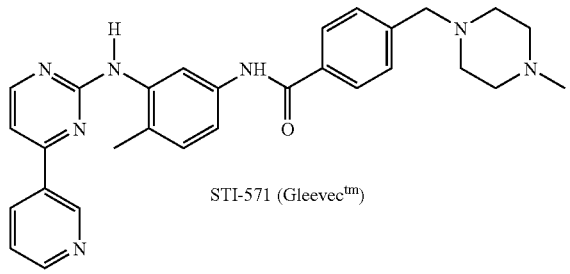

STI-571 (Gleevec™)

The present invention relates to the goal of preparing novel tyrosine kinase inhibitors that would be given alone or in combination with STI-571 to cancer patients since the cancerous cells should be less able to become resistant to all the drugs at once. In addition, novel active substances that would hit alternative targets and work alone or in synergy with STI-571 are also sought after targets.

OBJECTS OF THE INVENTION

It is an object of the invention to provide novel compounds which can be used to treat one or more of tumors, cancer and proliferative diseases as otherwise described herein.

It is an additional object of the invention to provide pharmaceutical compounds based upon the compounds disclosed herein.

It is yet another object of the invention to provide methods to treat patients for one or more of tumors, cancer, hyperproliferative diseases including psoriasis, genital warts and hyperproliferative cell growth diseases, including hyperproliferative keratinocyte diseases such as hyperkeratosis, ichthyosis, keratoderma or lichen planus.

It is still another object of the present invention to use the present compounds alone or synergistically with other anti-tumor/anti-cancer agents for the treatment of tumors and/or cancer in patients.

It is yet another object of the present invention to provide pharmaceutical compositions which may be advantageously used in combination with other anti-tumor/anti-cancer agents in the interest of providing synergistic therapy to patients in need of such therapy.

One or more of these and/or other objects of the invention will be readily apparent from a review of the disclosure of the present invention herein.

BRIEF DESCRIPTION OF THE FIGURES

FIGS. 5-12 show the effect of varying the chemical structure of a number compounds according to the present invention on biological activity.

FIG. 14 shows the effect of compounds on the number of viable cells.

SUMMARY OF THE INVENTION

Figure 1:
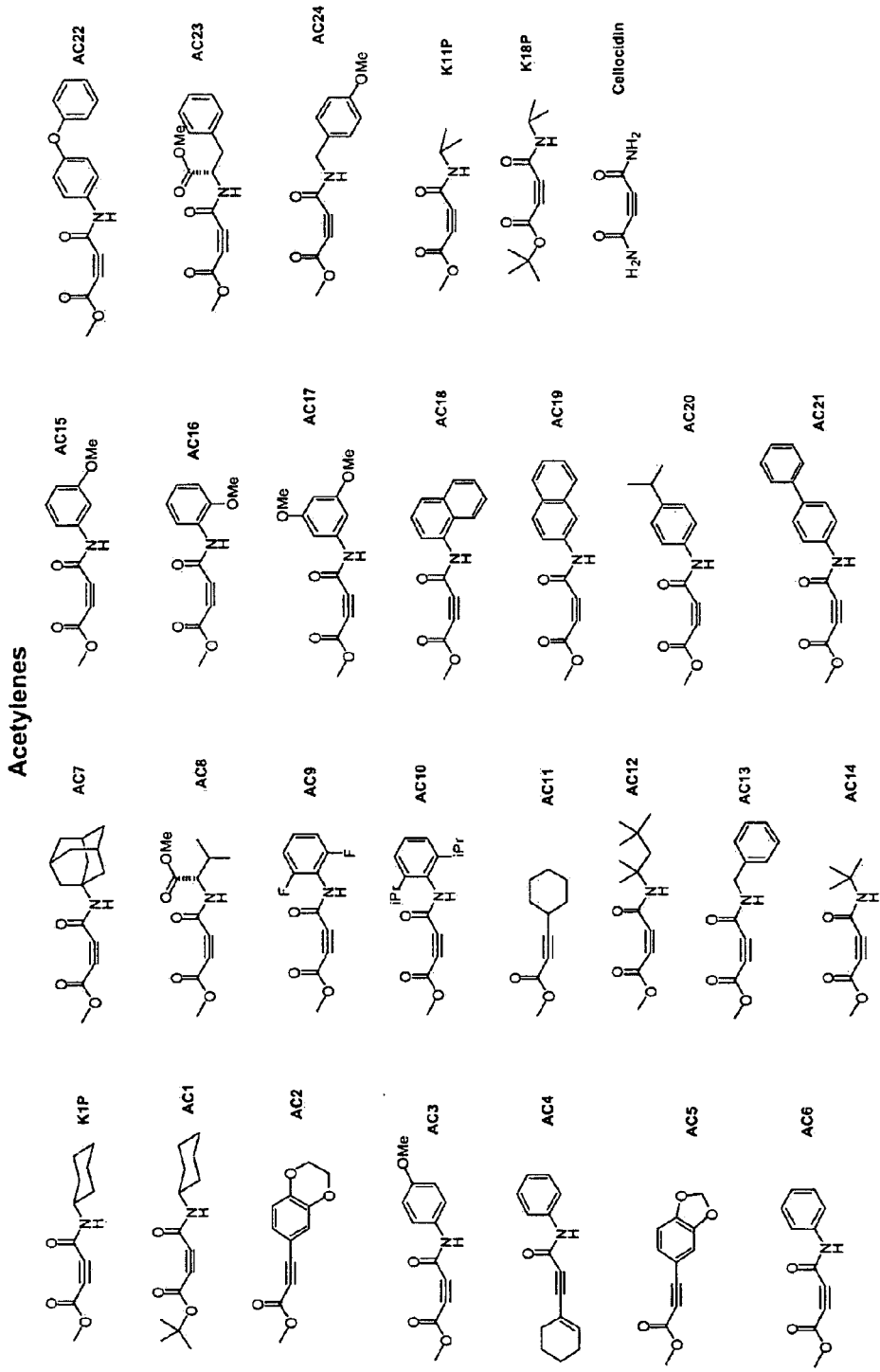
FIG. 1 depicts a number of representative compounds according to the present invention.

The present invention relates to compounds according to either of the structures set forth below:

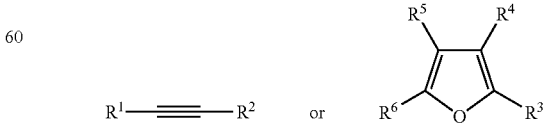

where $R^1$ is H, OH, F, Cl, Br, I, a $C_1$-$C_6$ optionally substituted alkyl or alkenyl group, an optionally substituted aryl group or a

group;

$R_a$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^2$ is a

group;

$R_b$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^3$ and $R^6$ are each independently selected from H, OH, F, Cl, Br, I, a $C_1$-$C_6$ optionally substituted alkyl or alkenyl group, an optionally substituted aryl group, a carbamate, alkylene carbamate, urethane or alkylene urethane;

$R^4$ is a

group, wherein $R_a$ is as described above; and $R^5$ is a

group, wherein $R_b$ is as described above, with the proviso that at least one of $R^1$ and $R^2$ or $R^4$ and $R^5$ contains an $R_a$ or $R_b$ group which is an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

or a stereoisomer, pharmaceutically acceptable salt, solvate, and polymorph thereof.

In preferred aspects of the present invention, the compounds according to the present invention contain at least one ester group and at least one amide group, preferably with each such group bonded directly to the acetylene or furan moieties, such that $R^1$ forms an ester group with the acetylenic group and $R^2$ forms an amide group with the acetylenic moiety. In the case of the furan compounds, $R^4$ preferably forms an amide group such that $R_b$ is preferably an amine or substituted amine group and $R^5$ preferably forms an ester group with the furan moiety, such that $R_a$ is preferably an O-alkyl or O-aryl group as otherwise defined hereinabove. These compounds are presented below.

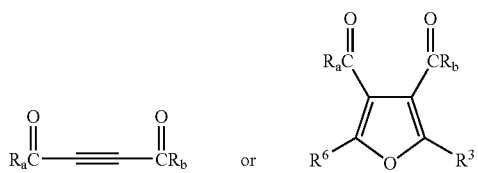

Pharmaceutical compositions based upon the above-described compounds comprise an effective amount of compound in combination with a pharmaceutically acceptable carrier, additive or excipient.

Other aspects of the present invention are directed to methods of treating tumors, cancer, hyperproliferative diseases including psoriasis, genital warts and hyperproliferative cell growth diseases, including hyperproliferative keratinocyte diseases such as hyperkeratosis, ichthyosis, keratoderma or lichen planus, the method comprising administering to a patient in need thereof an effective amount of a compound according to the formula:

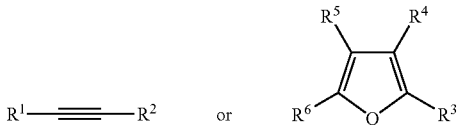

where $R^1$ is H, F, Cl, Br, I, a $C_1$-$C_6$ optionally substituted alkyl or alkenyl group, an optionally substituted aryl group or a

group;

$R_a$ is a $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^2$ is a

group;

$R_b$ is a $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^3$ and $R^6$ are each independently selected from H, F, Cl, Br, I, a $C_1$-$C_6$ optionally substituted alkyl or alkenyl group, an optionally substituted aryl group, a carbamate, alkylene carbamate, urethane or alkylene urethane;

$R^4$ is a

group, wherein $R_b$ is as described above, and $R^5$ is a

group, wherein $R_a$ is as described above;

with the proviso that at least one of $R^1$ and $R^2$ or $R^4$ and $R^5$ contains an $R_a$ or $R_b$ group which is an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

or a stereoisomer, pharmaceutically acceptable salt, solvate, and polymorph thereof in combination with a pharmaceutically acceptable carrier, additive or excipient.

DETAILED DESCRIPTION OF THE INVENTION

The following terms are used throughout the specification to describe the present invention:

"Patient" or "subject" is used throughout the specification to describe an animal, generally a mammalian animal, including a human, to whom treatment or use with the compounds or compositions according to the present invention is provided. For treatment or use with/or of those conditions or disease states which are specific for a specific animal (especially, for example, a human subject or patient), the term patient or subject refers to that particular animal.

"Alkyl" refers to a fully saturated monovalent hydrocarbon radical containing carbon and hydrogen which may be a straight chain, branched, or cyclic group. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl. "Cycloalkyl" groups refer to cyclic alkyl groups such as cyclopropyl, cyclobutyl, cyclopentyl and cyclohexyl. $C_1$-$C_7$ alkyl groups are preferably used in certain aspects of the present invention, although the alkyl group may be larger, in certain advantageous instances. The term alkyl also refers to monocyclic, bicyclic, tricyclic and tetracyclic alkyl (i.e., hydrocarbon) groups. Alkyl groups according to the present invention may be substituted or unsubstituted.

The term "alkenyl" refers to an alkyl group with at least one double bond between adjacent carbon atoms within the chemical group. The term "alkylene" refers to an optionally substituted group having the general formula —$(CH_2)_n$— where n is a positive integer from 1 to 12, preferably from 1 to 6, more preferably from 1 to 3.

The term "substituted" refers to a chemical group or moiety which occurs on (is bonded to) another group and may include one or more functional groups such an alkyl containing from 1 to 6 carbon atoms, preferably a lower alkyl containing 1-3 carbon atoms, aryl, substituted aryl, acyl, ester, halogen (i.e., alkyl halos, e.g., $CF_3$), hydroxy, alkoxy, carboxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like. Alkyl and ester groups, for example,

groups are preferred substituents in certain aspects of the present invention. Substituted, for example, as in "substituted alkyl" or "substituted alkenyl", means that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, and the like, as described above. When the term "substituted" appears prior to a list of possible substituted groups, it is intended that the term apply to every member of that group.

The term "aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as imidazolyl, furyl, pyrrolyl, pyridyl, thienyl and indolyl. The term "heteroaryl" refers to an aryl group which contains at least one atom selected from O, N and S.

"Halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Heterocycle" or "heterocyclic" refers to a carbocylic ring wherein one or more carbon atoms have been replaced with one or more heteroatoms such as nitrogen, oxygen or sulfur. A substitutable nitrogen on an aromatic or non-aromatic heterocyclic ring may be optionally substituted. The heteroatoms N or S may also exist in oxidized form such as NO, SO and $SO_2$. Examples of heterocycles include, but are not limited to, piperidine, pyrrolidine, morpholine, thiomorpholine, piperazine, tetrahydrofuran, tetrahydropyran, 2-pyrrolidinone, δ-velerolactam, δ-velerolactone and 2-ketopiperazine, among numerous others.

The term "biphenyl" refers to a group which contains two optionally substituted aryl groups, preferably phenyl groups, which are linked together at a single carbon atom on each phenyl group.

The terms "carbamate", "alkylene carbamate", "urethane" or "alkylene urethane" refers to a substituent or moiety which may be represented by the structure

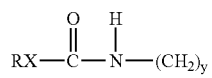

where R is a optionally substituted $C_1$-$C_8$ alkyl group or an aryl group, X is O (carbamate) or N (urethane) and y is from 0 to 6. Compounds according to the present invention based upon a furan skeleton may contain carbamates, alkylene carbamates, urethanes or alkylene urethanes as indicated at $R^3$ and $R^6$ of the furan ring.

The term "compound" is used herein to refer to any specific chemical compound disclosed herein. Within its use in context, the term generally refers to a single compound, but in certain instances may also refer to stereoisomers and/or optical isomers (including racemic mixtures) of disclosed compounds.

The term "effective amount" refers to the amount of a selected compound according to the present invention which is used in an amount to produce an intended effect within the context of its use and in particular, the treatment method to be used. The precise amount of a compound according to the present invention used in a given context will vary depending upon the particular compound selected and its intended use, the disease or condition to be treated, the method of delivery, the age and weight of the subject, route of administration, and so forth, but may be easily determined by routine experimentation. In the case of the treatment of a condition or disease state, an effective amount is that amount which is used to effectively treat the particular condition or disease state.

The term "pharmaceutically acceptable" refers to a carrier, additive or excipient which is not unacceptably toxic to the subject to which it is administered.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention.

The term "tumor" is used to describe a malignant or benign growth or tumefacent.

The term "hyperproliferative disease state" refers to a disease state in which cells are growing in an uncontrolled manner, whether that growth is cancerous or not. Such a disease state may be reflected in psoriasis or genital warts or other hyperproliferative cell growth diseases, including hyperproliferative keratinocyte diseases including hyperkeratosis, ichthyosis, keratoderma or lichen planus, all of which disease states may be treated using compounds according to the present invention.

The present invention includes the compositions comprising the pharmaceutically acceptable acid addition salts of compounds of the present invention. The acids which are used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)] salts, among others.

The invention also includes compositions comprising base addition salts of the present compounds. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e, calcium and magnesium), ammonium or water-soluble amine addition salts such as N-methylglucamine-(meglumine), and the lower alkanolammonium and other base salts of pharmaceutically acceptable organic amines, among others.

The compounds of this invention include all stereoisomers where relevant (i.e., cis and trans isomers) and all optical isomers of the present compounds (e.g., R and S enantiomers), as well as racemic, diastereomeric and other mixtures of such isomers, as well as all polymorphs of the compounds.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.5 milligram to about 750 milligrams, more preferably about 1 milligram to about 600 milligrams, and even more preferably about 10 milligrams to about 500 milligrams of active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Other aspects of the present invention are directed to methods of treating tumors, cancer, hyperproliferative diseases including psoriasis, genital warts and hyperproliferative cell growth diseases, including hyperproliferative keratinocyte diseases such as hyperkeratosis, ichthyosis, keratoderma or lichen planus, the method comprising administering to a patient in need thereof an effective amount of a compound according to the formula:

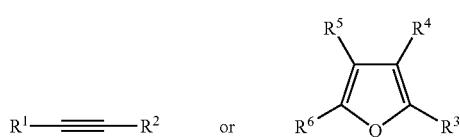

where $R^1$ is H, OH, F, Cl, Br, I, a $C_1$-$C_6$ optionally substituted alkyl or alkenyl group, an optionally substituted aryl group or a

group;

$R_a$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^2$ is a

group;

$R_b$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^3$ and $R^6$ are each independently selected from H, OH, F, Cl, Br, I, a $C_1$-$C_6$ optionally substituted alkyl or alkenyl group, or an optionally substituted aryl group;

$R^4$ is a

group, wherein $R_b$ is as described above; and $R^5$ is a

group, wherein $R_b$ is as described above, with the proviso that at least one of $R^1$ and $R^2$ or $R^4$ and $R^5$ contains an $R_a$ or $R_b$ group which is an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

or a stereoisomer, pharmaceutically acceptable salt, solvate, and polymorph thereof, optionally in combination with a pharmaceutically acceptable additive, carrier or excipient.

Representative compounds of the present invention can be readily synthesized in accordance with the general synthetic methods described below and are illustrated more particularly in the schemes that follow. Since the schemes are illustrative, the invention should not be construed as being limited by the chemical reactions and conditions expressed. The preparation of the various starting materials used in the schemes is well within the skill of persons versed in the art. Compounds not specifically mentioned may be readily synthesized by analogy following techniques and methods well known to those of skill in the art.

Unless specified to the contrary, reactions herein occur at approximately atmospheric pressure and at a temperature of between about 0° C. and the boiling point of any organic solvent used in the reaction. Inert organic solvents such as dichloromethane, diethyl ether, dimethylformamide, chloroform or tetrahydrofuran are preferred solvents in the reactions disclosed herein, although other solvents may be used where appropriate or indicated. Reaction times can range from about one hour to about forty-eight hours, and reactants optionally are stirred, shaken, or agitated. Reactions can be done in one pot or in steps, unless specified to the contrary.

General Chemistry and Structure Activity

Two scaffolds described hereafter preferably have been used: a planar scaffold, represented by compounds containing a furan core with various groups displayed at C-2, C-3, C-4 and C-5 of the furan and an acetylene core (structure index).

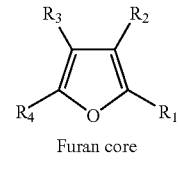

Furan core

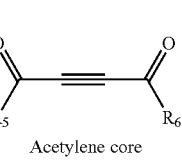

Acetylene core

Figure 2:
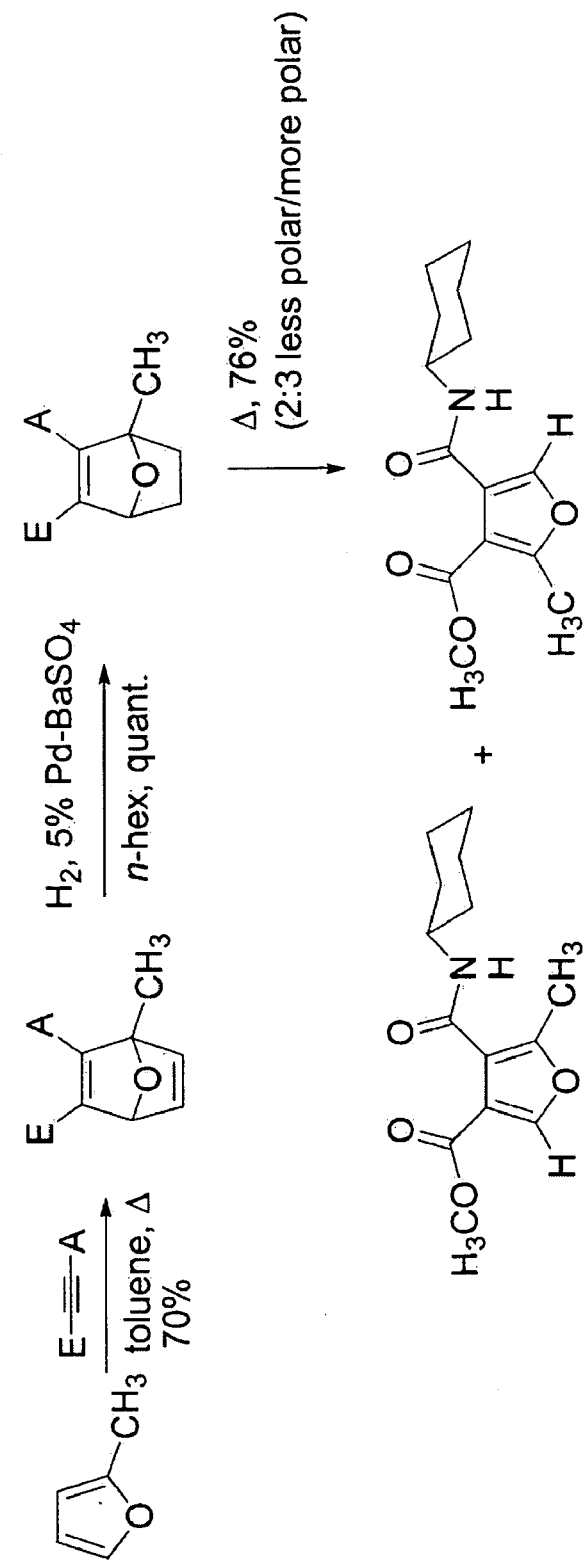
FIG. 2 depicts a chemical scheme directed to certain furan compounds according to the present invention.
Figure 3:
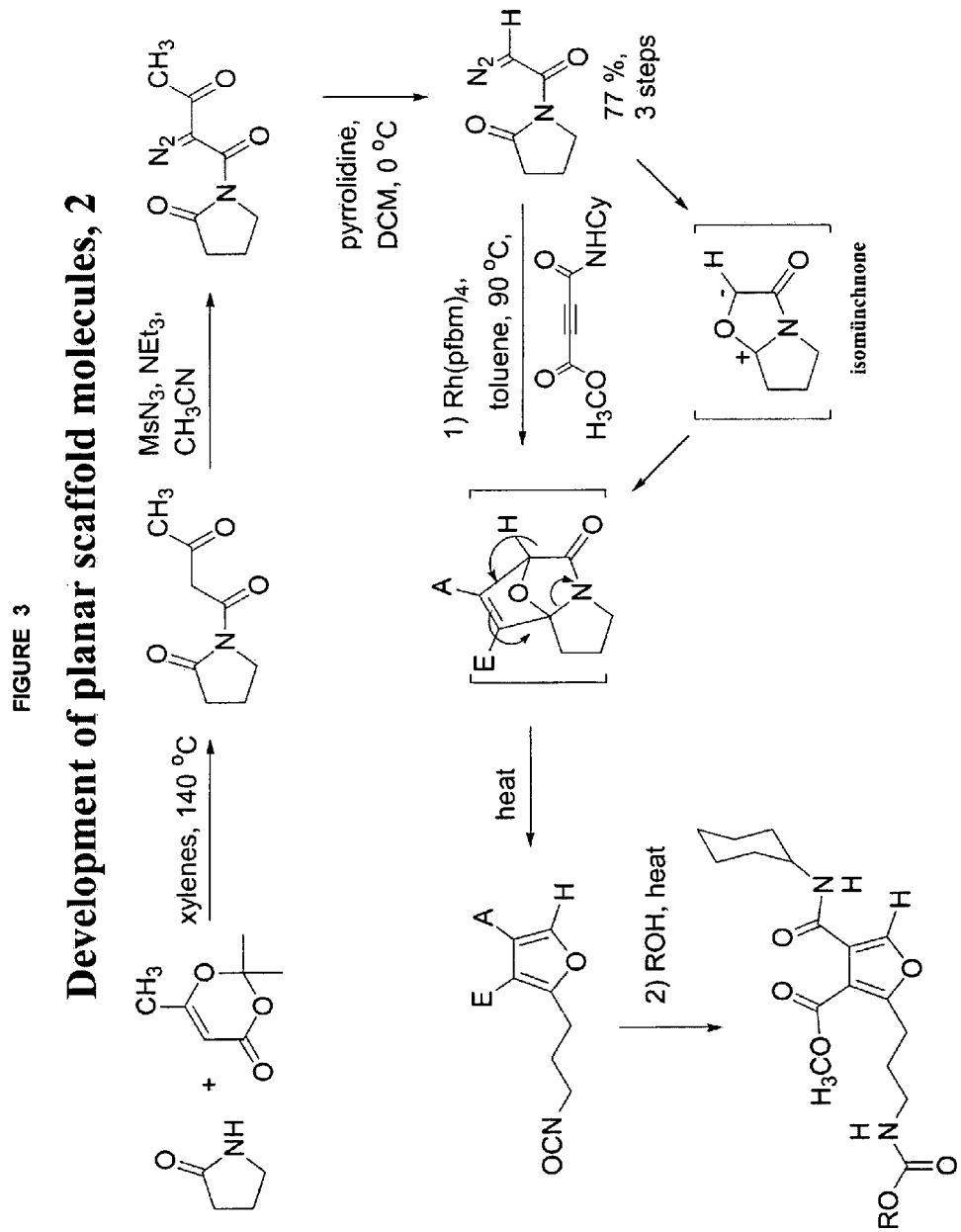
FIG. 3 depicts a chemical scheme directed to alternative furan compounds according to the present invention.

Some furans (R1=H or $CH_3$, R2=CONHCy or $CO_2CH_3$, R3=$CO_2CH_3$ or CONHCy, R4=$CH_3$ or H) were prepared by Diels-Alder cycloaddition of an acetylene bearing an amide and an ester group (R5 and R6) on each side of the triple bond, followed by regioselective reduction of the unsubstituted double bond and retro Diels-Alder reaction (FIG. 2). The other furans (R1=H, R2=CONHCy, R3=$CO_2CH_3$, R4=$CH_2CH_2CH_2NHCO_2R$ with R=$CH_3$, $(CH_2)_3CH_3$, $CH_2CH(CH_2CH_3)_2$, $CH_2CH(NHBoc)CH(CH_3)_2$, $CH_2Cy$, $CH_2Ph$) were prepared from pyrrolidinone after conversion to its corresponding imide, diazotransfer, deacylation, cycloaddition with an acetylene bearing an amide and an ester groups on each side of the triple bond, cycloreversion and heating with an alcohol (FIG. 3).

Figure 4:
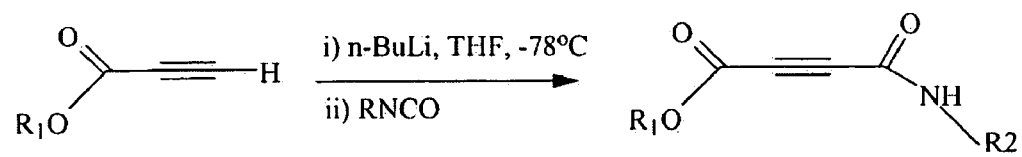
FIG. 4 shows a simple chemical scheme directed to the synthesis of acetylene compounds according to the present invention.

The acetylenes were prepared by deprotonation of a propiolate (either methyl or tert-butyl) with n-butyllithium and subsequent reaction with an isocyanate (FIG. 4). Modifications may be readily made following the aforementioned schemes. The furan and acetylene libraries were both tested for activity in a cell-based assay where the death of engineered murine myeloid cells (32D-bcr-abl), the survival of which depends on the activity of bcr-abl tyrosine kinase, was sought. The control cell line that enables the determination of the selectivity of the compounds is also a murine cell line, which does not depend on bcr-abl kinase activity to survive.

The biological activity of these compounds was evaluated in two ways, a murine cell line differential proliferation assay and a NCI 60 human carcinoma cell-line growth inhibition and cell death assay. The murine cell death assays were performed using a p210bcrabl transformed 32D murine cell line. This is a differential assay, measuring the ability of the molecule to selectively inhibit the transformed cells (32 Dbcrabl) over the non-transformed, growth factor dependent parental cell line (32D). The NCI assay was performed in the Developmental Therapeutics Program at the National Cancer Institute. This assay measures the inhibition of cell growth and cell death from sixty different human carcinomas. Both the acetylene and furan structural cores represent novel chemical entities with no prior reports of biological activity. Biological data collected thus far show that both the ester and amide moiety provide the greatest activity and are preferred. In addition, subtle changes in R1 confer major differences in biological activity, suggesting a specific cellular target for these molecules. The molecules K1P, AC19, AC22, AN7A and AN7B (FIG. 1) showed good activity against a number of carcinoma and model carcinoma cell lines. At present, the use of these compounds is to be preferred in the treatment of tumors and cancer.

Biological and Structure Activity

The furan and acetylene libraries were both tested for activity in a cell-based assay where the death of engineered murine myeloid cells (32D-bcr-abl), the survival of which is depends on the activity of bcr-abl tyrosine kinase, was sought. The control cell line that enables the determination of the selectivity of the compounds is also a murine cell line, which does not depend on bcr-abl kinase activity to survive.

Figure 6:
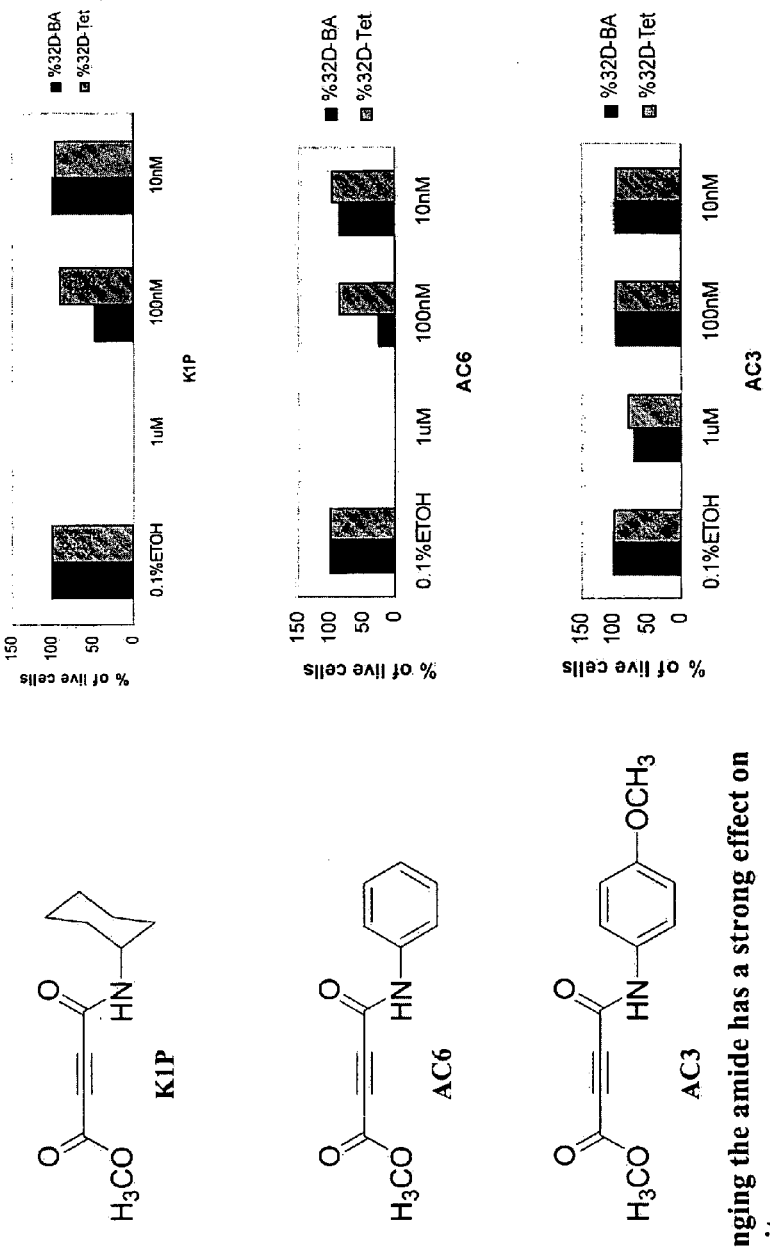

We have found that a carbonyl on either side of the triple bond was clearly preferred for activity since compounds AC2, AC4, AC5 and AC11 showed little or no activity (see structure index in FIG. 1). Investigation of the importance of the ester on activity, compounds K1P and AC1 were compared. As seen in FIG. 5, the two compounds performed equally well in the assay in terms of activity and selectivity. At 100 nM, the compounds are still active with 50% of leukemic cells surviving and 100% of the control cells surviving. The optimization was therefore continued at the amide site. The ester can be later modified to improve the pharmacokinetic properties of the future drug. Investigation of the scaffold right side was then carried out as shown in FIG. 6. Changing the amide group from cyclohexylamide (K1P) to phenylamide (AC6) increased both selectivity and activity while adding an electron donating group at the para position of the aromatic ring (AC3) decreased activity and selectivity dramatically. The position of substitution on the ring was further tested with compounds AC15, AC16, and AC17. It was found that activity was regained at the 1 uM level in the case of the ortho, meta and di-meta substitution while selectivity remained low (FIG. 7). FIG. 8 shows the effect of the nature of the substituent on the phenyl ring and revealed that two electron withdrawing groups such as fluorine at the ortho position (AC9) rendered the molecule inactive while two bulky inductive group such as isopropyl groups (AC10) had moderate activity but no selectivity. Adding an extra methylene unit between the phenyl ring and the amide nitrogen gave an active benzylamide compound (AC13) with little selectivity. These cell assays were usually carried out using 50 cell/well in average and FIG. 8 shows the result of an assay that used a varying number of cells per well, while keeping the concentration of the compound constant at 1 uM. Complete selectivity and activity was observed at 2000 cells per well. Using the phenylamide (AC6) as a lead, acetylenes AC19, AC21 and AC22 were designed and prepared to explore the space available for binding on the amide side. As seen FIG. 9, these 3 new compounds all exhibit excellent activity at 100 nM but only AC19 shows selectivity. Next a combination of STI-571 and compounds AC22 and AC19 was tested. FIG. 10 shows that STI-571 is moderately active (30% of the myeloid engineered murine cells are killed but the all the control cells are still alive) and selective at 10 nM in our assay while AC22 is very active but not selective at 100 nM and not active at 10 nM. As a combination, however, AC22 and STI-571 show complete activity and 70% selectivity, while at 10 nM the activity remains and the selectivity is enhanced to 100%. Neither of these compounds, on its own, displays such activity and selectivity, therefore it seems that a combination of AC22 and STI-571 act in synergy to combat leukemic cells while being non toxic to control cells. A different result is obtained with AC19, which, in combination with STI-571 does not increase the activity or selectivity compared to STI-571 alone. This suggests that AC19 and STI-571 might be acting with the same target while AC22 and STI-571 might bind to different sites thereby showing a multiplicative effect of either compound (FIG. 11).

Figure 12:
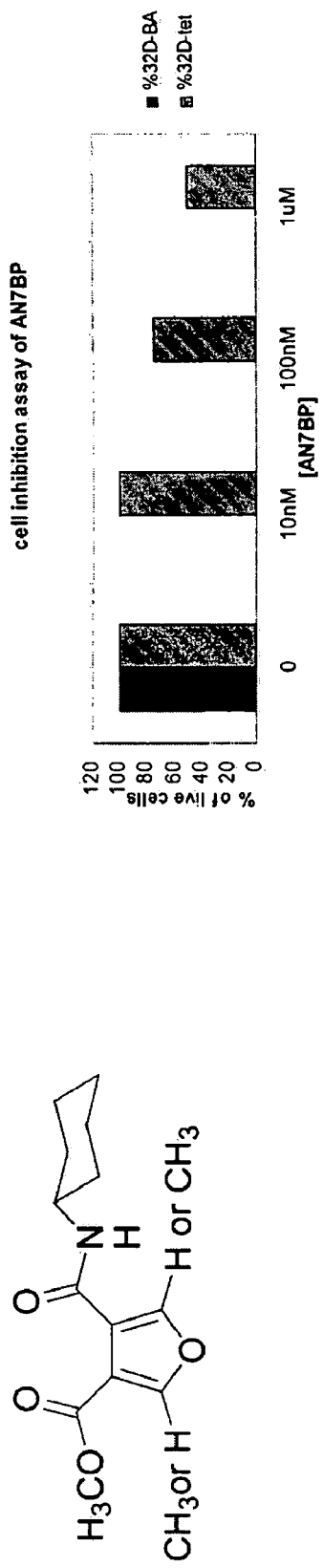

Furans AN7A and AN7B were also evaluated for activity and selectivity in our assay and showed incredible activity and selectivity (both 100% at 10 nM); the graph shown in FIG. 12 corresponds to the cell assay results for furan AN7B. In order to obtain additional information about the behavior of our compounds in cancerous cells, 18 compounds were submitted to and accepted by the NCI for testing on 60 human carcinoma cell lines as set forth in the examples section. This would confirm the activity seen in our cell-based assay and maybe give an insight into the mechanism of action and biological target of the acetylene/furan compounds. While the results were somewhat disappointing (AC19 did not show activity below 10 uM and AC22 showed mediocre growth inhibition between 2.6 and 7.3 uM in leukemia cell lines only), K1P had an interesting pattern of activity whereby it inhibited growth of leukemia cell lines (GI50 between 0.8 and 5 uM) and renal cell lines (GI50: 2.5 uM to 2.7 uM). As a result, K1P was singled out by the NCI for further testing: MTD (Maximum Tolerated Dose) and murine hollow fiber in vivo assay. These are being carried out at the present time, along with testing of furans AN7A and AN7B in the 60 human cancer cell lines.

The invention is described further in the following examples, which are illustrative and in no way limiting.

EXAMPLES

In order to access a representative range of compounds using commercially available starting materials, the general strategy for the preparation of the acetylenes involved the deprotonation of methyl propiolate with n-butyllithium (1.6M in hexanes) at −78° C. followed by addition of the desired isocyanate, source of the diversity at the amide moiety. It was found that the use of 1.05 eq of n-BuLi gave a cleaner product than the use of 1.5 eq. Also, for compounds of preparation type 2 (from AC14 onwards), it was found that stirring for a reduced amount of time increased the yield.

The final compounds were obtained in moderate to high yields (23-84%). Purification of these compounds was found difficult; they were generally purified by careful column chromatography followed by recrystallisation. In some case, HPLC purification was also required.

General Experimental Conditions $^1$H— and $^{13}$C— nuclear magnetic spectra (NMR) were recorded as solutions in deuteriated chloroform (CDCl$_3$) unless stated otherwise with tetramethylsilane as the internal reference, on a DPX-400 MHz or 500 MHz Brucker Avance FT-NMR spectrometer. Chemical shift values (δ) are given in part per million (ppm) and coupling constants (J) are expressed in Hertz (Hz). Mass spectra were recorded at the UIUC School of chemical Science and were obtained by electron ionisation (EI) technique. Elemental analyses were performed by Atlantic Microlab, Inc. Routine analytical thin layer chromatography (TLC) was carried out on J. T. Baker Si250 F$_{254}$ glass-backed plates. The plates were developed with the appropriate solvent system and visualized either by UV lamp or dipping into Hanessian stain and heating with a heat gun. Column chromatography was carried out using 230-400 mesh, 60 A, silica gel from Silicycle. Reagents were obtained from Aldrich, Sigma or Fluka. High performance liquid chromatography was performed on a Varian Chrompack Microsorb-MV 100-5 C-18 column (250×4.6× ¼" mm) using Varian Prostar 210-SDM pumps with an isocratic mixture of methanol and water (80:20); UV detection was at 254 nm with a Varian Prostar 320-U/VIS detector. Solvents were Analar grade except for THF, which was puriss grade (H$_2$O<0.005%) and used without further purification. When mixed solvent systems were used, the ratios are v/v. When ethyl acetate and hexanes are used as a mixture, the percentage given is in ethyl acetate (i.e. ethyl acetate-hexanes 5%).

Type 1 Procedure for the Preparation of Acetylenes

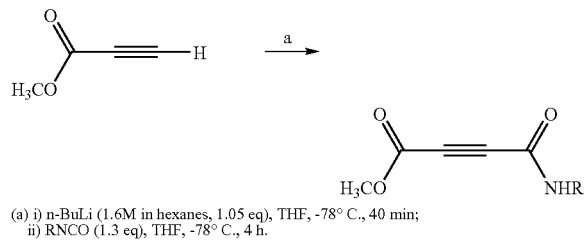

(a) i) n-BuLi (1.6M in hexanes, 1.05 eq), THF, -78° C., 40 min;
ii) RNCO (1.3 eq), THF, -78° C., 4 h.

A solution of methyl propiolate (0.445 ml, 5 mmol) in dry THF (25 ml) was cooled to −78° C. under N$_2$, before a solution of n-butyllithium (1.6M in hexanes, 3.3 ml, 5.25 mmol) was added dropwise. The mixture was stirred at that temperature for 40 min before the isocyanate (6.5 mmol) was added dropwise. The resulting reaction mixture was allowed to stir at −78° C. for 4 h. Trimethylsilyl chloride (2 ml) was added and the mixture was stirred for a further 30 min prior to addition of aqueous hydrochloric acid (1N, 6.5 ml) and the reaction mixture was allowed to warm to room temperature. The resulting two phases were separated and the aqueous layer was extracted with ethyl acetate (3×20 ml). The combined organic extracts were dried over sodium sulfate, filtered and concentrated in vacuo to give an oil which was purified by column chromatography.

Type 2 Procedure for the Preparation of Acetylenes

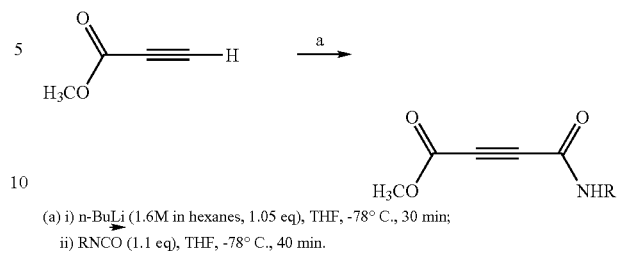

(a) i) n-BuLi (1.6M in hexanes, 1.05 eq), THF, -78° C., 30 min;
ii) RNCO (1.1 eq), THF, -78° C., 40 min.

A solution of methyl propiolate (0.445 ml, 5 mmol) in dry THF (25 ml) was cooled to −78° C. under N$_2$, before a solution of n-butyllithium (1.6M in hexanes, 3.3 ml, 5.25 mmol) was added dropwise. The mixture was stirred at that temperature for 30 min before the isocyanate (5 mmol) was added dropwise. The resulting reaction mixture was allowed to stir at −78° C. for 30 min. A saturated aqueous solution of ammonium chloride (20 ml) was added and the mixture was allowed to warm to room temperature. The resulting two phases were separated and the aqueous layer was extracted with ethyl acetate (3×20 ml). The combined organic extracts were washed with saturated aqueous sodium hydrogen carbonate (20 ml), dried over magnesium sulfate, filtered and concentrated in vacuo to give an oil which was purified by column chromatography. The resulting crystalline compounds were recrystallised from hexanes and ethyl acetate.

Characterization of Compounds Used for Comparison:

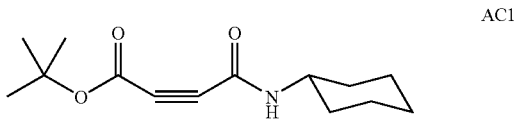

AC1

76% yield; R$_f$ 0.3 (hex/EA 4:1); (Found C, 66.82; H, 8.49; N, 5.60; O, 19.04; C$_{14}$H$_{21}$NO$_3$ requires C, 66.91; H, 8.42; N, 5.57; O, 19.10); (retention time minutes, seconds); $^1$H-NMR (400 MHz, CDCl$_3$) 5.66 (1H, br s), 3.85-3.81 (1H, m), 1.93 (2H, dd, J 12.6, 3.5), 1.71-1.70 (2H, m), 1.54 (1H, m), 1.50 (9H, s), 1.37-1.35 (2H, m) and 1.18-1.15 (3H, m); $^{13}$C-NMR (100 MHz, CDCl$_3$) 151.3 (C$_q$), 150.1 (C$_q$), 85.1 (C$_q$), 75.4 (C$_q$), 74.8 (C$_q$), 49.1 (CH), 32.6 (2×CH$_2$), 27.9 (3×CH$_3$), 24.9 (CH$_2$) and 24.6 (CH$_2$); m/z (EI) 251.152206 (M$^+$, C$_{14}$H$_{21}$NO$_3$ requires 251.152144), 251 (M$^+$, 5%), 152 (MH$^+$-CO$_2$$^t$Bu, 47), 114 (100), 98 (12) and 83 (30).

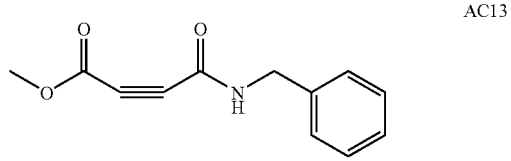

AC13

48% yield; R$_f$ (hex/EA); (Found C, 66.24; H, 5.04; N, 6.44; O, 21.98; C$_{12}$H$_{11}$NO$_3$ requires C, 66.35; H, 5.10; N, 6.45; O, 22.10); (retention time 3 minutes, 57 seconds); $^1$H-NMR (400 MHz, CDCl$_3$) 7.38-7.27 (5H, m), 6.2 (1H, br s), 4.62 (2H, d, J 5.9) and 3.82 (3H, s); $^{13}$C-NMR (100 MHz, CDCl$_3$) 152.6 (C$_q$), 150.5 (C$_q$), 136.4 (C$_q$), 129.0, 128.2, 128.0 and 127.3 (5×CH), 77.2 (C$_q$), 73.9 (C$_q$), 53.4 (CH$_3$)

and 44.1 (CH₂); m/z (EI) 217.074208 (M⁺, C₁₂H₁₁NO₃ requires 217.073893), 217 (M⁺, 23%), 159 (MH⁺-CO₂Me, 68) and 106 (PhNH⁺, 100).

Characterization of Other Compounds:

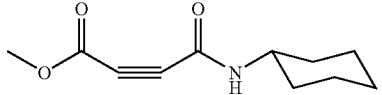

K1P

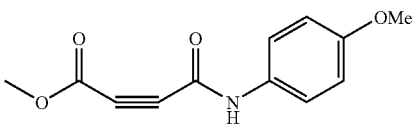

AC3

66% yield; R$_f$ 0.15 (hex/EA, 4:1); (Found C, 63.12; H, 7.13; N, 6.64; O, 23.07; C₁₁H₁₅NO₃ requires C, 63.14; H, 7.22; N, 6.70; O, 22.94); (retention time 2 minutes, 56 seconds); ¹H-NMR (500 MHz, CDCl₃) 5.98 (1H, br s), 3.86-3.84 (1H, m), 3.83 (3H, s), 1.95-1.92 (2H, m), 1.74-1.70 (2H, m), 1.61-1.57 (1H, m), 1.37-1.35 (2H, m) and 1.19-1.17 (2H, m); ¹³C-NMR (125 MHz, CDCl₃) 152.8 (C$_q$), 149.7 (C$_q$), 77.9 (C$_q$), 73.2 (C$_q$), 53.3 (CH₃), 49.3 (CH), 32.6, 25.3 and 24.6 (5×CH₂); m/z (EI) 209.1045986 (M⁺, C₁₁H₁₅NO₃ requires 209.105194), 209 (M⁺, 6%), 166 (44) and 128 (100).

100%; R$_f$ 0.1 (hex/EA, 4:1); (Found C, 61.74; H, 4.87; N, 6.02; O, 27.51; C₁₂H₁₁NO₄ requires C, 61.80; H, 4.75; N, 6.01; O, 27.44); (retention time 3 minutes, 31 seconds); 1H-NMR (400 MHz, CDCl₃) 8.47 (1H, br s), 7.45 (2H, d, J 12.5), 6.88 (2H, d, J 12.5), 3.86 (3H, s) and 3.80 (3H, s); ¹³C-NMR (100 MHz, CDCl₃) 157.3 (C$_q$), 152.7 (C$_q$), 148.0 (C$_q$), 129.5 (C$_q$), 121.9 (CH), 114.3 (CH), 77.6 (C$_q$), 74.1 (C$_q$), 55.5 (CH₃), 53.5 (CH₃); m/z (EI) 233.069052 (M⁺, C₁₂H₁₁NO₄ requires 233.068808), 233 (M⁺, 7%), 122 (15) and 62 (100).

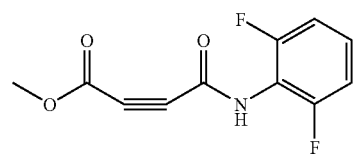

AC6

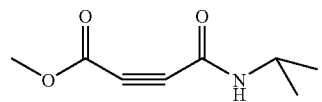

K11P

71% yield; R$_f$ (hex/EA); (retention time 3 minutes, 32 seconds); ¹H-NMR (400 MHz, CDCl₃) 7.59 (1H, br s), 7.51 (2H, d, J 7.7), 7.36-7.32 (2H, m), 7.18 (1H, m) and 3.86 (3H, s); ¹³C-NMR (100 MHz, CDCl₃); m/z (EI) 203.058896 (M⁺, C₁₁H₉NO₃ requires 203.058243), 203 (M⁺, 64%), 172 (M⁺-OMe, 35) and 145 (MH⁺-CO₂Me, 100).

68% yield; R$_f$ 0.16 (hex/EA, 4:1); (Found C, 56.59; H, 6.53; N, 8.16; O, 28.64; C₈H₁₁NO₃ requires C, 56.80; H, 6.55; N, 8.28; O, 28.37); (retention time 3 minutes, 5 seconds); ¹H-NMR (400 MHz, CDCl₃) 5.84 (1H, br s), 4.18-4.07 (1H, m), 3.83 (3H, s) and 1.20 (6H, d, J 6.5); ¹³C-NMR (100 MHz, CDCl₃) 152.8 (C$_q$), 149.7 (C$_q$), 77.7 (C$_q$), 73.1 (C$_q$), 53.4 (CH₃), 45.5 (CH) and 22.3 (2×CH₃); m/z (EI) 169.073537 (M⁺, C₈H₁₁NO₃ requires 169.073893), 169 (M⁺, 17%), 154 (M⁺-Me, 100), 138 (M⁺-OMe, 16) and 111 (MH⁺-CO₂Me, 61).

AC9

33% yield; R$_f$ (hex/EA); (retention time 2 minutes, 58 seconds); dodgy ¹H-NMR (400 MHz, CDCl₃) 7.32-7.25 (2H, m), 7.08-6.97 (2H, m), 3.88 (3H, s) and 3.80 (1H, br s); ¹³C-NMR (100 MHz, CDCl₃) get peak labels on spectrum; m/z (EI) 239.039140 (M⁺, C₁₁H₇F₂NO₃ requires 239.039400), 239 (M⁺, 100%), 220 (M⁺-F, 59) and 203 (M⁺-OMe, 62).

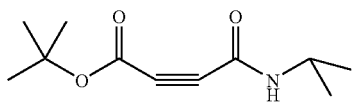

K18P

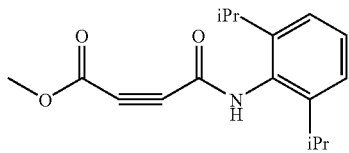

AC10

84% yield; R$_f$ (hex/EA); (Found C, 65.59; H, 8.12; N, 6.66; O, 22.93; C₁₁H₁₇NO₃ requires C, 62.54; H, 8.11; N, 6.63; O, 22.72); (retention time 3 minutes, 39 seconds); ¹H-NMR (400 MHz, CDCl₃) 5.77 (1H, br s), 4.17-4.07 (1H, m), 1.50 (9H, s) and 1.19 (6H, d, J 6.5); ¹³C-NMR (100 MHz, CDCl₃) 151.2 (C$_q$), 150.2 (C$_q$), 85.1 (C$_q$), 75.3 (C$_q$), 74.7 (C$_q$), 42.4 (CH), 27.9 (3×CH₃) and 22.3 (CH₃); m/z (EI) 211.121045 (M⁺, C₁₁H₁₇NO₃ requires 211.120844), 211 (M⁺, 4%), 196 (M⁺-Me, 19), 155 (MH⁺-$^t$Bu, 44), 140 (M⁺-$^t$Bu-Me, 100) and 111 (MH⁺-$^t$Bu-$^i$Pr).

80% yield; R$_f$ 0.26 (hex/EA, 4:1); (Found C, 70.88; H, 7.22; N, 4.88; O, 16.49; C₁₇H₂₁NO₃ requires C, 71.06; H, 7.37; N, 4.87; O, 16.70); (retention time 2 minutes, 13 seconds); dodgy, doris' ¹H-NMR (300 MHz, CDCl₃) 7.22-

7.20 (3H, m), 3.90 (3H, s), 3.05 (2H, m) and 1.17 (12H, 2×d, J 7.0); $^{13}$C-NMR (75 MHz, CDCl$_3$) 147.3 (C$_q$×2), 146.3 (C$_q$×2), 129.4 (C$_q$), 124.0 (CH×3), 77.6 (C$_q$), 67.6 (C$_q$), 53.6 (CH$_3$), 29.0 (CH$_3$), 28.8 (CH$_3$) and 23.7 (CH); m/z (EI) 287.151570 (M$^+$, C$_{17}$H$_{21}$NO$_3$ requires 287.152144), 287 (M$^+$, 52%), 255 (MH$^+$-OMe, 57), 240 (100) and 212 (92).

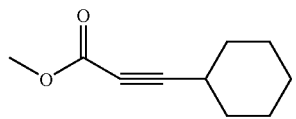

AC11

% yield; R$_f$ (hex/EA); (retention time minutes, seconds); $^1$H-NMR (400 MHz, CDCl$_3$); $^{13}$C-NMR (100 MHz, CDCl$_3$); m/z (EI) (M$^+$, CHNO requires).

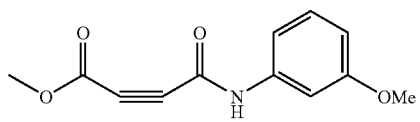

AC15

50% yield; R$_f$ 0.1 (hex/EA, 4:1); (retention time 3 minutes, 31 seconds); $^1$H-NMR (400 MHz, CDCl$_3$) 8.47 (1H, br s), 7.45 (2H, d, J 12.5), 6.88 (2H, d, J 12.5), 3.86 (3H, s) and 3.80 (3H, s); $^{13}$C-NMR (100 MHz, CDCl$_3$) 157.3 (C$_q$), 152.7 (C$_q$), 148.0 (C$_q$), 129.5 (C$_q$), 121.9 (CH), 114.3 (CH), 77.6 (C$_q$), 74.1 (C$_q$), 55.5 (CH$_3$), 53.5 (CH$_3$); m/z (EI) 233.069052 (M$^+$, C$_{12}$H$_{11}$NO$_4$ requires 233.068808), 233 (M$^+$, 7%), 122 (15) and 62 (100).

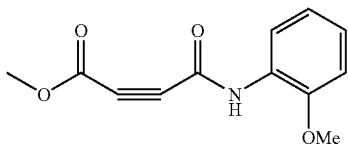

AC16

56% yield; R$_f$ 0.44 (hex/EA, 1:1); (retention time 3 minutes, 27 seconds); $^1$H-NMR (400 MHz, CDCl$_3$) 8.28 (1H, dd, J 1.4, 8), 8.21 (1H, br s), 7.11 (1H, apparent dt, J 1.5, 7.7), 6.97 (1H, dt, J 0.9, 8.7), 6.90 (1H, d, J 8.2), 3.91 (3H, s) and 3.87 (3H, s); $^{13}$C-NMR (100 MHz, CDCl$_3$) 153.2 (C$_q$), 148.1 (2×C$_q$), 126.9 (C$_q$), 125.7 (CH), 121.5 (CH), 120.9 (CH), 110.5 (CH), 78.1 (C$_q$), 74.1 (C$_q$), 56.2 (CH$_3$) and 53.8 (CH$_3$); m/z (EI) 233.068297 (M$^+$, C$_{12}$H$_{11}$NO$_4$ requires 233.068808), 233 (M$^+$, 100%), 218 (M$^+$-Me, 3), 202 (M$^+$-OMe, 25) and 175 (MH$^+$-CO$_2$Me, 40).

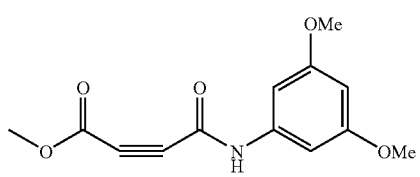

AC17

30% yield; R$_f$ (hex/EA); (retention time 3 minutes, 42 seconds); $^1$H-NMR (500 MHz, CDCl$_3$) 7.69 (1H, br s), 6.73 (2H, s), 6.30 (1H, s), 3.86 (3H, s) and 3.79 (6H, s); $^{13}$C-NMR (125 MHz, CDCl$_3$) 161.2 (2×C$_q$), 152.6 (C$_q$), 148.1 (C$_q$), 138.2 (C$_q$), 95.5 (2×CH), 97.9 (CH), 77.4 (C$_q$), 74.1 (C$_q$), 55.5 (2×CH$_3$) and 53.5 (CH$_3$); m/z (EI) 263.079901 (M$^+$, C$_{13}$H$_{13}$NO$_5$ requires 263.079373), 263 (M$^+$, 31%), 235 (45), 232 (M$^+$-OMe, 35), 204 (M$^+$-CO$_2$Me, 100).

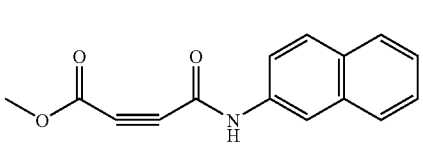

AC19

81% yield; R$_f$ 0.14 (hex/EA, 4:1); (retention time 3 minutes, 26 seconds); $^1$H-NMR (400 MHz, CDCl$_3$) 8.21 (1H, s), 7.95-7.79 (3H, m), 7.70 (1H, br s), 7.51-7.42 (3H, m) and 3.92 (3H, s); $^{13}$C-NMR (100 MHz, CDCl$_3$) 153.2 (C$_q$), 148.8 (C$_q$), 134.5 (C$_q$), 133.9 (C$_q$), 131.5 (C$_q$), 129.5, 128.3, 128.0, 127.2, 126.2, 119.8 and 118.1 (7×CH), 78.1 (C$_q$), 74.7 (C$_q$), 53.9 (CH$_3$); m/z (EI) 253.074299 (M$^+$, C$_{15}$H$_{11}$NO$_3$ requires 253.073893), 253 (M$^+$, 67%), 222 (M$^+$-OMe, 22), 195 (MH$^+$-CO$_2$Me, 28), 115 (100).

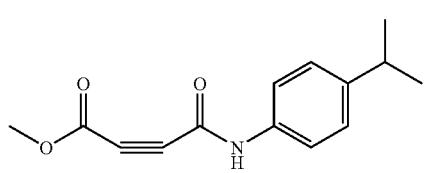

AC20

48% yield; R$_f$ 0.11 (hex/EA, 4:1); (retention time 5 minutes, 53 seconds); $^1$H-NMR (500 MHz, CDCl$_3$) 7.63 (1H, br s), 7.41 (2H, d, J 8.5), 7.19 (2H, d, J 8.5), 3.86 (3H, s), 2.93-2.86 (1H, m) and 1.23 (6H, d, J 4.5); $^{13}$C-NMR (125 MHz, CDCl$_3$) 152.9 (C$_q$), 148.2 (C$_q$), 146.6 (C$_q$), 134.4 (C$_q$), 127.1 and 120.2 (4×CH), 77.2 (C$_q$), 74.0 (C$_q$), 53.5 (CH$_3$), 33.7 (CH) and 23.9 (CH$_3$×2); m/z (EI) (M$^+$, CHNO requires).

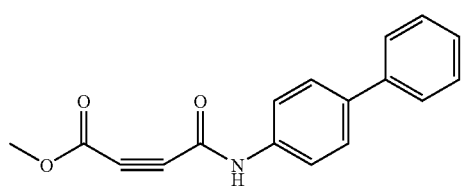

AC21

26% yield; R$_f$ (hex/EA); (Found C, 73.14; H, 4.85; N, 5.05; O, 17.00; C$_{17}$H$_{13}$NO$_3$ requires C, 73.11; H, 4.69; N, 5.01; O, 17.19); $^1$H-NMR (500 MHz, CDCl$_3$) 7.67 (1H, br s), 7.59-7.55 (6H, m), 7.46-7.42 (2H, m), 7.37-7.33 (1H, m) and 3.88 (3H, s); $^{13}$C-NMR (125 MHz, CDCl$_3$) 153.2 (C$_q$), 148.6 (C$_q$), 140.5 (C$_q$), 138.9 (C$_q$), 136.2 (C$_q$), 129.3, 128.2, 127.8, 127.3 and 120.9 (9×CH), 77.9 (C$_q$), 74.7 (C$_q$) and 53.9 (CH$_3$); m/z (EI) 279.088946 (M$^+$, C$_{17}$H$_{13}$NO$_3$ requires 279.089543), 279 (M$^+$, 100%), 193 (62), 168 (65) and 141 (70).

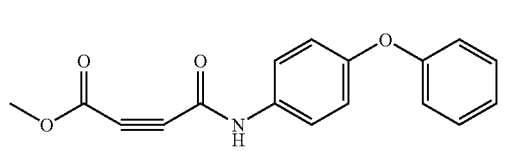

AC22

50% yield; $R_f$ (hex/EA); (Found C, 70.21; H, 4.32; N, 5.19; $C_{17}H_{13}NO_4$ requires C, 69.15; H, 4.44; N, 4.74; O, 21.67); (bad HPLC); $^1$H-NMR (500 MHz, CDCl$_3$) 7.53 (1H, br s), 7.49 (2H, d, J 7.9), 7.35 (2H, app t, J 7.5), 7.11 (1H, app t, J 7.5), 7.0 (4H, d J 7.5) and 3.87 (3H, s); $^{13}$C-NMR (125 MHz, CDCl$_3$) 157.0 ($C_q$), 154.7 ($C_q$), 152.7 ($C_q$), 148.2 ($C_q$), 131.8 ($C_q$), 129.9, 129.8, 123.5, 121.9, 119.4, 119.0 and 118.8 (9×CH), 77.5 ($C_q$), 74.3 ($C_q$) and 53.5 (CH$_3$); m/z (EI) 295.084774 (M$^+$, $C_{17}H_{13}NO_4$ requires 295.084458).

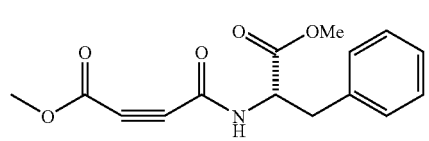

AC23

7% yield; $R_f$ 0.15 (hex/EA, 4:1); (retention time 3 minutes, 27 seconds); $^1$H-NMR (500 MHz, CDCl$_3$) 7.32-7.25 (3H, m), 7.09 (2H, d, J 8.2), 6.66 (1H, d, J 1.4), 4.90 (1H, app dt, J 5.7, 7.8), 3.81 (3H, s), 3.74 (3H, s), 3.19 (1H, dd, J 5.7, 18.7) and 3.11 (1H, dd, J 5.7, 14); $^{13}$C-NMR (125 MHz, CDCl$_3$) 171.1 ($C_q$), 153.0 ($C_q$), 150.4 ($C_q$), 135.4 ($C_q$), 129.9, 129.6, 129.1, 128.0 and 127.8 (5×CH), 77.7 ($C_q$), 74.5 ($C_q$), 57.5 (CH$_3$), 54.1 (CH$_3$), 53.1 (CH) and 37.9 (CH$_2$); m/z (EI) (M$^+$, CHNO requires).

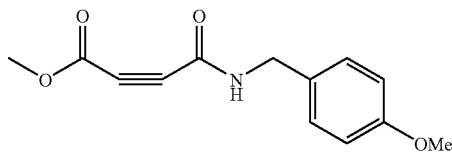

AC24

27% yield; $R_f$ 0.44 (hex/EA, 1:1); (retention time 3 minutes, 26 seconds); $^1$H-NMR (500 MHz, CDCl$_3$) 7.20 (2H, d, J 8.6), 6.88 (2H, d, J 8.6), 6.23 (1H, br s), 4.42 (2H, d, J 5.8), 3.81 (3H, s) and 3.80 (3H, s); $^{13}$C-NMR (125 MHz, CDCl$_3$) 159.5 ($C_q$), 152.7 ($C_q$), 150.4 ($C_q$), 129.4 (CH×2), 128.5 ($C_q$), 114.3 (2×CH), 77.3 ($C_q$), 73.8 ($C_q$), 55.3 (CH$_3$), 53.3 (CH$_3$) and 43.7 (CH$_2$); m/z (EI) 247.084683 (M$^+$, $C_{13}H_{13}NO_4$ requires 247.084458), 247 (M$^+$, 56%), 217 (MH$^+$-OMe, 40), 189 (MH$^+$-CO$_2$Me, 40), 136 (M$^+$-CO-tp-CO$_2$Me, 100), 121 (OMePhCH$_2^+$, 92).

Preparation of the Furan Library (K1 and K2):

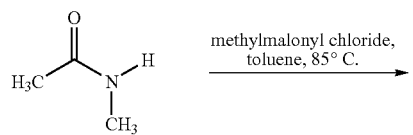

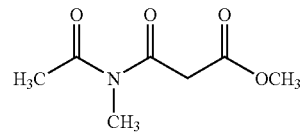

N-methylacetamide (1.00 g, 13.68 mmol) was dissolved in toluene (75 ml) and stirred at room temperature before methyl malonyl chloride (1.9 ml, 17.78 mmol) was added slowly. Nitrogen was bubbled through the reaction mixture, which was heated to 85° C. for 4 h. Upon cooling, diethyl ether (20 ml) was added and the reaction mixture was washed with sat. aq. sodium bicarbonate and sat. aq. sodium chloride solutions. The organic phase was dried with sodium sulfate, filtered and evaporated to dryness to afford a yellow liquid (1.72, 72%), which was used without further purification.

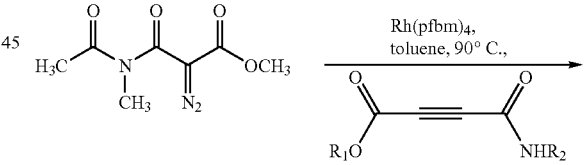

Triethylamine (2.1 ml, 15 mmol) was added to a solution of imide X (0.86 g, 5 mmol) in THF (20 ml) and methanesulfonyl azide (0.9 g, 7.5 mmol). The reaction mixture was left to stir at room temperature overnight before concentration in vacuo. Purification by column chromatography (gradient elution from 10% to 40% EA/hex) gave a yellow oil (0.71 g, 71%).

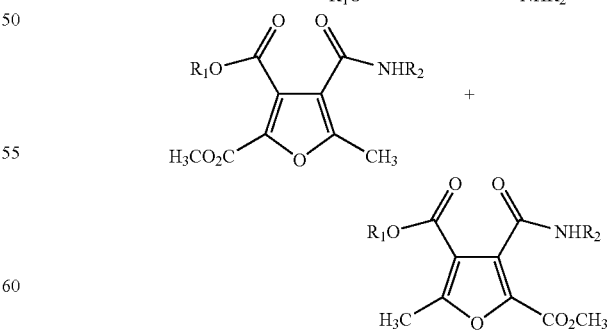

The diazoimide (132 mg, 0.66 mmol) was combined with the acetylene (1.0 mmol) and rhodium perfluorobutyramidate (2.5 mg) in dry toluene (4 ml). The reaction mixture was allowed to stir at room temperature overnight then heated to 90° C. for 8 h. Evaporation of the solvent gave a yellow oil, which was purified by column chromatography (10% up to 50% EA/hex).

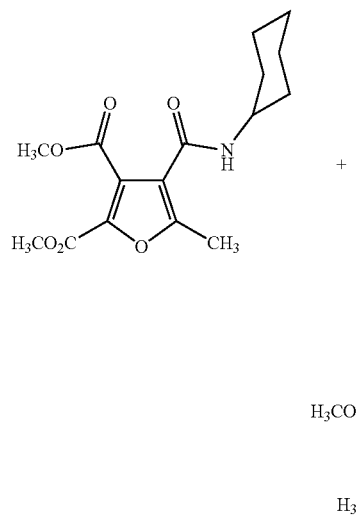

K1 and K2 less polar 16% yield; $R_f$ 0.52 (50% EA/hex); $^1$H-NMR (300 MHz, CDCl$_3$) 7.04 (1H, br s), 3.94 (3H, s), 3.92 (3H, s), 3.88 (1H, m), 2.64 (3H, s), 1.94-1.92 (2H, m), 1.70-1.62 (3H, m), 1.44-1.31 (2H, m), 1.27-1.12 (3H, m); $^{13}$C-NMR (75 MHz, CDCl$_3$) Doris' data.

K2 (More Polar)

39% yield; $R_f$ 0.22 (50% EA/hex); $^1$H-NMR (300 MHz, CDCl$_3$) 5.95 (1H, br s), 3.90 (3H, s), 3.88 (3H, s), 3.83 (1H, m), 2.64 (3H, s), 2.03-2.00 (2H, m), 1.76-1.71 (2H, m), 1.61 (1H, m), 1.43-1.36 (2H, m), 1.27-1.22 (3H, m); $^{13}$C-NMR (75 MHz, CDCl$_3$) Doris' data.

Preparation of the Furan Library with a 3-methylene Unit at the 5-Position

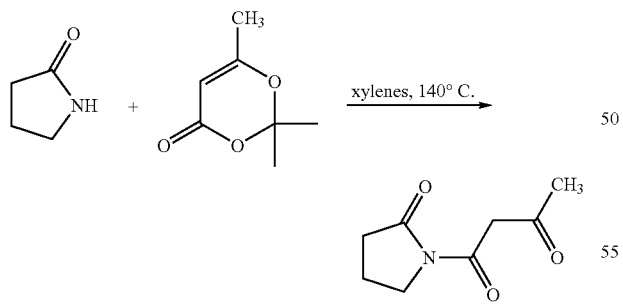

A solution containing 2-pyrrolidinone (1.33 ml, 17.51 mmol) and 2,2,6-trimethyl-1,3-dioxen-4-one (2.75 ml, 21.1 mmol) in xylenes (17.5 ml) was heated to reflux under a nitrogen atmosphere for 2 h. The solvent was removed under vacuum to give a brown oil, which was purified by column chromatography (5:1 hex/EA) affording the desired compound as a transparent oil that solidified in the freezer (2.82 g, 96%).

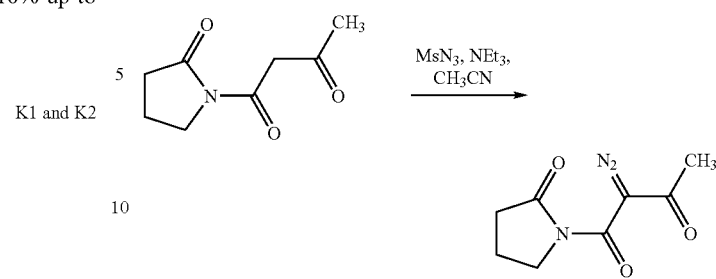

Triethylamine (3.0 ml, 21.3 mmol) was added to a solution of b-ketoimide (1.8 g, 10.6 mmol) and methanesulfonyl azide (1.55 g, 12.8 mmol) in acetonitrile (6 ml) at room temperature. The reaction mixture was stirred overnight and the solvent was removed under reduced pressure. The resulting residue was purified by column chromatography (20% EA/hex) to give 1.99 g (96%) of the desired product as a yellow oil.

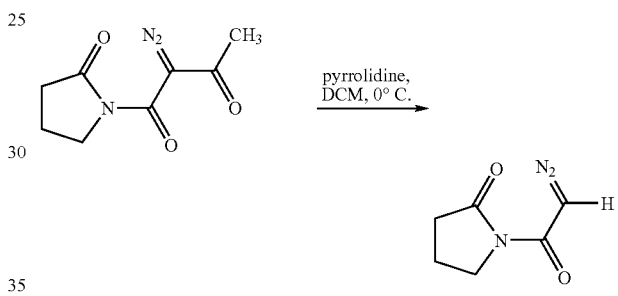

Pyrrolidine (2.14 ml, 25.64 mmol) was added dropwise to a solution containing the diazoimide (1 g, 5.1 mmol) in dichloromethane (12 ml) at 0° C. under nitrogen atmosphere. The resulting solution was stirred at 0° C. for 2 h. before the solvent was removed under vacuum. The residue thereby obtained was purified by column chromatography (1:2 EA/hex) to give the desired product in 80% yield (632.4 g).

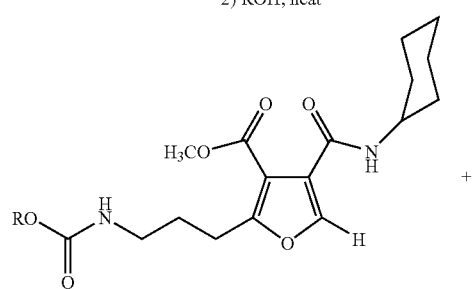

-continued

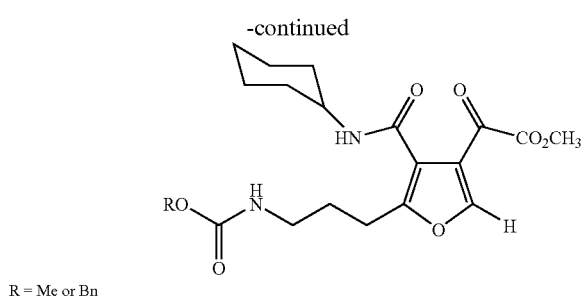

R = Me or Bn

A solution of acetylene (168 mg, 0.80 mmol) and rhodium perfluorobutyramidate (cat) in toluene (1.5 ml) was heated to 95° C. under a nitrogen atmosphere. A solution of the diazoimide (112 mg, 0.73 mmol) in toluene (1.5 ml) was then added dropwise over 25 min. The solution was heated to reflux for 2 h. before it was cooled to room temperature and the solvent was evaporated under reduced pressure. The residue, typically yellow-brown was then dissolved in methanol (excess) and heated under reflux for 30 min. Upon cooling, the alcohol evaporated in vacuo and its corresponding residue was purified by column chromatography to give a pale yellow oil.

Nucleophile=methanol: 13% yield;

Nucleophile=benzylalcohol: 26% yield;

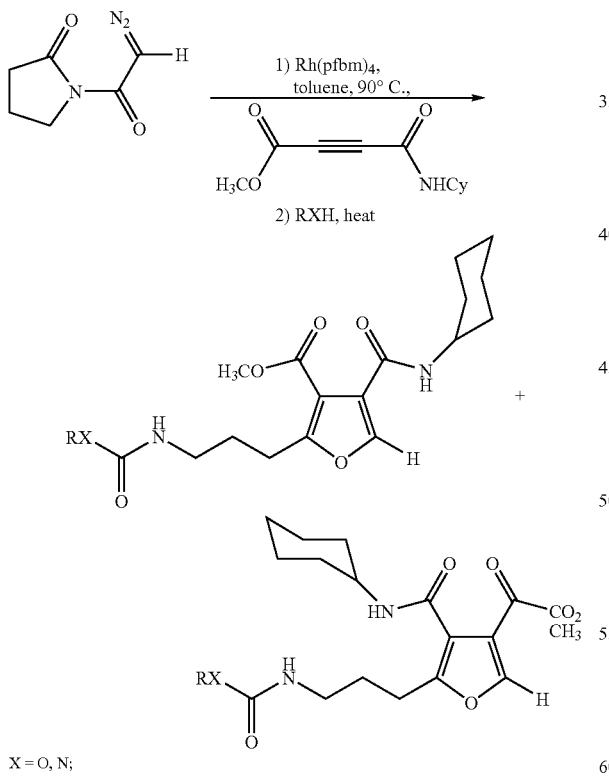

X = O, N;

A solution of acetylene (168 mg, 0.80 mmol) and rhodium perfluorobutyramidate (cat) in toluene (1.5 ml) was heated to 95° C. under a nitrogen atmosphere. A solution of the diazoimide (112 mg, 0.73 mmol) in toluene (1s.5 ml) was then added dropwise over 25 min. The solution was heated to reflux for 2 h. before it was cooled to room temperature and a nucleophile (excess) and heated under reflux for 30 min. Upon cooling, the solvent evaporated in vacuo and its corresponding residue was purified by column chromatography to give a pale yellow oil.

Nucleophile=allylamine; 23% yield;

Nucleophile=2-ethyl-1-butanol; 13% yield;

Nucleophile=1-butanol; 19% yield;

Nucleophile=N-Boc L-valinol; 14% yield;

Nucleophile=cyclohexanol; 16% yield;

Nucleophile=N-Boc L-phenylalaminol; % yield;

Nucleophile=allylalcohol;

AN7A and AN7B

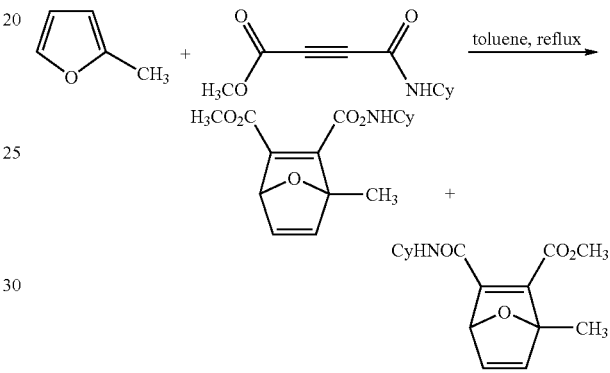

2-Methylfuran (0.5 ml, 5.49 mmol) was added to a solution of the acetylene (1 g, 4.77 mmol) in toluene (5 ml) and the resulting solution was heated to reflux for 3 h before the solvent was evaporated under vacuum. The resulting residue was purified by column chromatography (40% EA/hex) to give the product as a yellow oil (1.1 g, 80%).

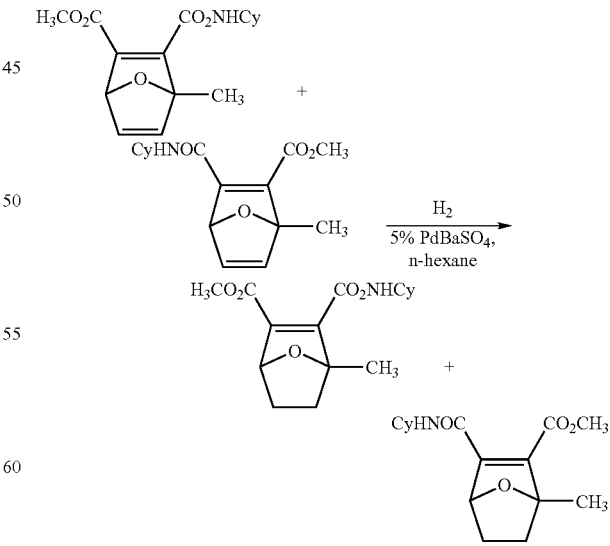

The mixture of regioisomers (700 mg, 2.4 mmol) in n-hexane (7 ml) was added to a stirred suspension of PdBaSO$_4$ (cat) in n-hexane. The mixture was degassed extensively and placed under hydrogen atmosphere at 0° C. The reaction was followed closely by analysis of aliquots. After 30 min, the reaction was complete and the mixture was filtered through a pad of celite® and evaporated to give the desired compound as a transparent oil (700 mg, quant.).

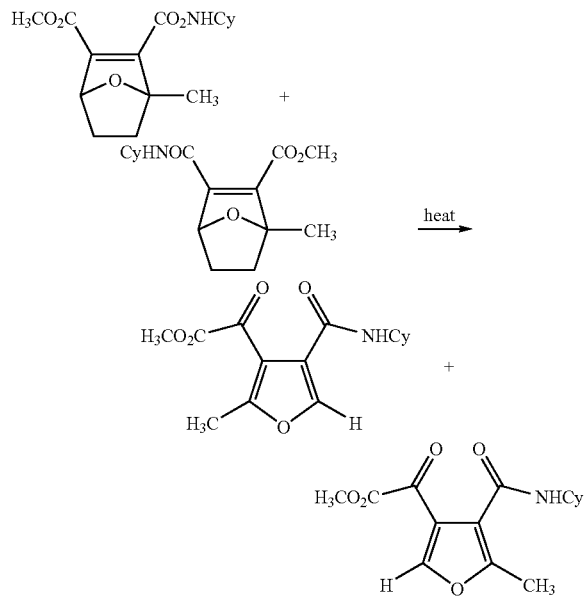

The mixture of regioisomers was heated to give, after column chromatography purification (5% to 20% EA/hex), the two expected furans. The less polar furan was obtained in 20%, the most polar furan in 32% and a mixture of both in 25%. The furans could be further purified by HPLC (80% MeOH/H2O, C18 column).

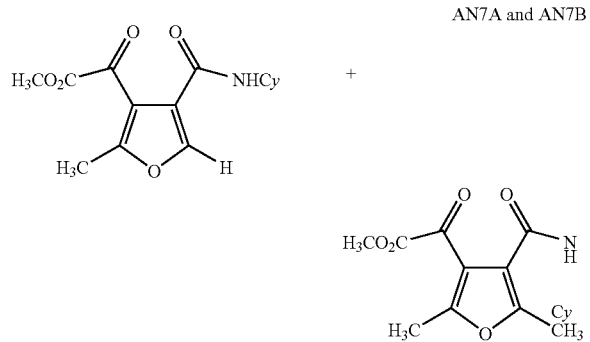

AN7A and AN7B less polar: $R_f$ 0.5 (hex/EA 3:2); (Found C, 63.17; H, 7.23; N, 5.24; $C_{14}H_{19}NO_4$ requires C, 63.38; H, 7.22; N, 5.28); (retention time 7 minutes, 27 seconds); $^1$H-NMR (400 MHz, CDCl$_3$) 9.23 (1H, br s), 7.90 (1H, s), 3.94-3.89 (1H, m), 3.87 (3H, s), 2.68 (3H, s), 1.99-1.96 (2H, m), 1.77-1.73 (2H, m), 1.55-1.54 (1H, m) and 1.43-1.31 (5H, m); $^{13}$C-NMR (100 MHz, CDCl$_3$); m/z (EI); more polar $R_f$ 0.4 (hex/EA 3:2); (Found C, 63.45; H, 7.24; N, 5.27; $C_{14}H_{19}NO_4$ requires C, 63.38; H, 7.22; N, 5.28); (retention time 6 minutes, 14 seconds); $^1$H-NMR (400 MHz, CDCl$_3$) 9.22 (1H, br s), 7.95 (1H, s), 3.96-3.92 (1H, m), 3.90 (3H, s), 2.57 (3H, s), 1.99-1.95 (2H, m), 1.76-1.72 (2H, m), 1.58 (1H, m) and 1.43-1.31 (5H, m); $^{13}$C-NMR (100 MHz, CDCl$_3$); m/z (EI)

Biological Testing

A number of compounds according to the present invention were tested for activity using the following three systems: a low cell density high throughput cell proliferation assay, a high cell density proliferation assay and a cell free kinase inhibition assay as described below. Activity was exhibited with several compounds according to the present invention consistent with these compounds being used in the treatment of tumors, cancer and other cell growth proliferation assays.

Low cell density high throughput cell proliferation assay Between 50 and 100 32D and 32DtetP210Bcr-Abl cells in 100 microliters of medium without serum were exposed to the test compound for 15 minutes. An equal volume of 20% serum supplemented tissue culture medium was then added and the cells were inoculated in single well in 32 wells of a 96 well plate. The endpoint of the assay was the fraction of the 32 wells in which a cell pellet was seen to develop which was filled with live cells. This assay is subject to automated screening by a plate reader for the cell pellet. We used this high throughput assay to screen for compounds that suppress the growth of the 32DtetP210Bcr-Abl cell line in the absence of IL-3, but allow the growth of the 32D cell line in the presence of IL-3. Various concentrations of each compound were tested. If a compound suppressed the growth of the P210Bcr-Abl cell line without affecting the growth of the 32D cell line, then the compound was considered to be selectively inhibitory for the P210Bcr-Abl dependent growth.

Figure 13:
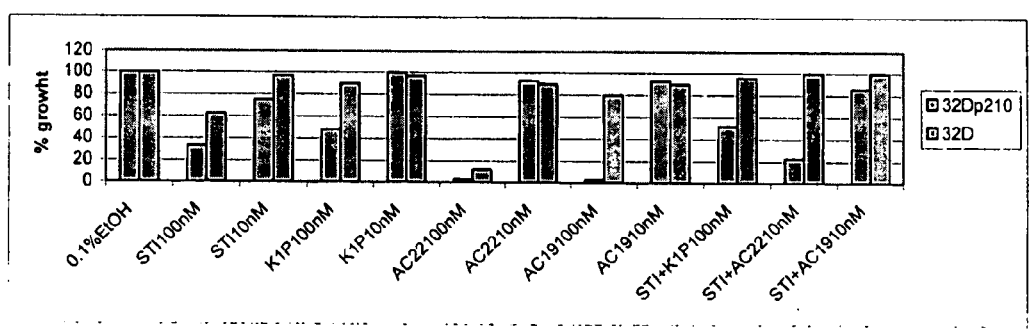
FIG. 13 shows the effect of compounds on cell growth.

As shown in FIG. 13, the compounds derived from the linear acetylene compounds, AC22 and K1P, are inhibitory to the 32DtetP210bcrabl cell line at 1 micromolar. AC22 also inhibits the 32Dtet cell line at a similar concentration. The effect of these compounds were also studied in combination with Imatinib (Gleevec or STI-571) to determine whether the compound had an additive or synergistic effect with Imatinib in inhibiting P210bcrabl dependent cell growth. As shown above, the inhibition of the combination of AC19 and Imatinib (STI571) at a concentration of 10 nanomolar of each drug (15% inhibition) is less than the sum of the inhibitory effect of both drugs alone (25%). When compound AC22 or K1P are added in combination with Imatinib to the culture of the 32DtetP210bcrabl cell line at 10 nanomolar concentration of both drugs, there is inhibition of the growth of the P210bcrabl dependent proliferation (80%) This is greater than the sum of the inhibition that is seen when the drugs (Imatinib inhibits 25% and AC22 inhibits 10%) are used separately. A similar synergism is seen for K1P and AC19: 45% inhibition together and 25% when used alone.

High Cell Density Cell Proliferation Assay (MTS)

This cell proliferation assay was performed using MTS tetrazolium (Cell titer96 Aqueous; Promega, Madison, Wis.), which measure numbers of viable cells. Between $2 \times 10^3$ and $2 \times 10^4$ STI-resistant cells are washed twice in RF-10 and plated in quadruplicate in the wells of a microtiter plate in 100 μl of RF-10 medium supplemented with various doses of test compounds (See FIG. 14). Controls using the same concentration of Imatinib without cells were set up in parallel. The plate is then incubated for 72 hours at 37 C in a humidified 5% CO$_2$ atmosphere. Twenty microliters of MTS were then added to the wells and the plate was incubated for three hours. Then the absorbance was recorded at 490-nm wavelength with a microplate autoreader (Spectramax). Results are expressed as the mean optical density of the 4-well set of each compound dose. All experiments were repeated at least 3 times.

Compounds identified as being selectively inhibitor for P210BcrAbl growth in the low density assay were also tested in a high cell density assay in which the number of cells was closer to that present in the blood stream in the presence of serum. This high cell density assay was not used to screen drugs initially but was used for in depth studies of compounds that were selected on the basis of the low cell density assay.

Cell Free Kinase Inhibition Assay. A panel of 60 kinases (Upstate Biotechnologies, Lake Placid, N.Y.) were analyzed in in vitro cell free kinase assays. The results for those kinases with associated inhibition are shown below.

| Kinase | % Inhibition at 10 μM* | |
|---|---|---|
| | K1P | AC22 |
| CaMKII | — | 40 |
| CaMKIV | — | 64 |
| CDK2/cyclinA | — | 50 |

-continued

| Kinase | % Inhibition at 10 μM* | |
|---|---|---|
| | K1P | AC22 |
| CK1 | 46 | (37) |
| Fyn | 49 | (29) |
| IKKBeta | — | 45 |
| Lyn | — | 98 |
| PKCγ | — | 61 |
| PKCbII | (35) | 48 |

*only % of inhibition >45% is reported

Testing of Compounds According to the Present Invention by NCI

The following cells lines were used to test the activity of compounds according to the present invention.

| Cell Line Name | Panel Name | Cell Number | Panel Number | Inoculation Density |
|---|---|---|---|---|
| CCRF-CEM | Leukemia | 3 | 7 | 40000 |
| HL-60(TB) | Leukemia | 8 | 7 | 15000 |
| K-562 | Leukemia | 5 | 7 | 5000 |
| MOLT-4 | Leukemia | 6 | 7 | 30000 |
| RPMI-8226 | Leukemia | 10 | 7 | 30000 |
| SR | Leukemia | 19 | 7 | 20000 |
| A549/ATCC | Non-Small Cell Lung Cancer | 4 | 1 | 7500 |
| EKVX | Non-Small Cell Lung Cancer | 8 | 1 | 20000 |
| HOP-18 | Non-Small Cell Lung Cancer | 27 | 1 | 20000 |
| HOP-19 | Non-Small Cell Lung Cancer | 28 | 1 | 20000 |
| HOP-62 | Non-Small Cell Lung Cancer | 26 | 1 | 10000 |
| HOP-92 | Non-Small Cell Lung Cancer | 29 | 1 | 20000 |
| NCI-H226 | Non-Small Cell Lung Cancer | 13 | 1 | 20000 |
| NCI-H23 | Non-Small Cell Lung Cancer | 1 | 1 | 20000 |
| NCI-H322M | Non-Small Cell Lung Cancer | 17 | 1 | 20000 |
| NCI-H460 | Non-Small Cell Lung Cancer | 21 | 1 | 7500 |
| NCI-H522 | Non-Small Cell Lung Cancer | 3 | 1 | 15000 |
| LXFL 529 | Non-Small Cell Lung Cancer | 30 | 1 | 10000 |
| DMS 114 | Small Cell Lung Cancer | 9 | 2 | 20000 |
| DMS 273 | Small Cell Lung Cancer | 11 | 2 | 5000 |
| SHP-77 | Small Cell Lung Cancer | 13 | 2 | 40000 |
| COLO 205 | Colon Cancer | 10 | 4 | 15000 |
| DLD-1 | Colon Cancer | 11 | 4 | 5000 |
| HCC-2998 | Colon Cancer | 2 | 4 | 10000 |
| HCT-116 | Colon Cancer | 3 | 4 | 5000 |
| HCT-15 | Colon Cancer | 15 | 4 | 10000 |
| HT29 | Colon Cancer | 1 | 4 | 5000 |
| KM12 | Colon Cancer | 17 | 4 | 15000 |
| KM20L2 | Colon Cancer | 18 | 4 | 10000 |
| SW-620 | Colon Cancer | 9 | 4 | 10000 |
| SF-268 | CNS Cancer | 14 | 12 | 15000 |
| SF-295 | CNS Cancer | 15 | 12 | 10000 |
| SF-539 | CNS Cancer | 16 | 12 | 15000 |
| SNB-19 | CNS Cancer | 2 | 12 | 15000 |
| SNB-75 | CNS Cancer | 5 | 12 | 20000 |
| SNB-78 | CNS Cancer | 6 | 12 | 20000 |
| TE671 | CNS Cancer | 10 | 12 | 20000 |
| U251 | CNS Cancer | 9 | 12 | 7500 |
| XF 498 | CNS Cancer | 17 | 12 | 20000 |
| LOX IMVI | Melanoma | 1 | 10 | 7500 |
| MALME-3M | Melanoma | 2 | 10 | 20000 |
| M14 | Melanoma | 14 | 10 | 15000 |
| RPMI-7951 | Melanoma | 3 | 10 | 20000 |
| M19-MEL | Melanoma | 16 | 10 | 10000 |
| SK-MEL-2 | Melanoma | 5 | 10 | 20000 |
| SK-MEL-28 | Melanoma | 8 | 10 | 10000 |
| SK-MEL-5 | Melanoma | 7 | 10 | 10000 |
| UACC-257 | Melanoma | 21 | 10 | 20000 |
| UACC-62 | Melanoma | 20 | 10 | 10000 |

| Cell Line Name | Panel Name | Cell Number | Panel Number | Inoculation Density |
|---|---|---|---|---|
| IGROV1 | Ovarian Cancer | 10 | 6 | 10000 |
| OVCAR-3 | Ovarian Cancer | 1 | 6 | 10000 |
| OVCAR-4 | Ovarian Cancer | 2 | 6 | 15000 |
| OVCAR-5 | Ovarian Cancer | 3 | 6 | 20000 |
| OVCAR-8 | Ovarian Cancer | 5 | 6 | 10000 |
| SK-OV-3 | Ovarian Cancer | 11 | 6 | 20000 |
| 786-0 | Renal Cancer | 18 | 9 | 5000 |
| A498 | Renal Cancer | 13 | 9 | 20000 |
| ACHN | Renal Cancer | 23 | 9 | 10000 |
| CAKI-1 | Renal Cancer | 15 | 9 | 10000 |
| RXF 393 | Renal Cancer | 16 | 9 | 15000 |
| RXF-631 | Renal Cancer | 17 | 9 | 10000 |
| SN12C | Renal Cancer | 8 | 9 | 15000 |
| SN12K1 | Renal Cancer | 10 | 9 | 10000 |
| TK-10 | Renal Cancer | 24 | 9 | 15000 |
| UO-31 | Renal Cancer | 4 | 9 | 15000 |
| P388 | Leukemia | 1 | 7 | 5000 |
| P388/ADR | Leukemia | 2 | 7 | 5000 |
| PC-3 | Prostate Cancer | 1 | 11 | 7500 |
| DU-145 | Prostate Cancer | 3 | 11 | 10000 |
| MCF7 | Breast Cancer | 1 | 5 | 5000 |
| NCI/ADR-RES | Breast Cancer | 2 | 5 | 15000 |
| MDA-MB-231/ATCC | Breast Cancer | 5 | 5 | 20000 |
| HS 578T | Breast Cancer | 6 | 5 | 20000 |
| MDA-MB-435 | Breast Cancer | 11 | 5 | 15000 |
| MDA-N | Breast Cancer | 12 | 5 | 15000 |
| BT-549 | Breast Cancer | 13 | 5 | 20000 |
| T-47D | Breast Cancer | 14 | 5 | 20000 |
| MAXF 401 | Breast Cancer | 16 | 5 | 20000 |
| MDA-MB-468 | Breast Cancer | 18 | 5 | 20000 |
| SK-BR-3 | Breast Cancer | 10 | 5 | 20000 |

Results showed that the compound KIP exhibited enhanced activity against certain leukemia cell lines, colon cancer cell lines, melanoma cell lines, renal cancer cell lines and a breast cancer cell line, thus showing the potential for broad activity of the compound K1P as well as other compounds according to the present invention.

While the invention has been described with reference to specific methods and embodiments, it will be appreciated that various modifications may be made without departing from the invention.

We claim:

1. A compound according to the structure:

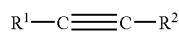

where $R^1$ is an optionally substituted

group;

$R_a$ is a H, OH, a $C_1$-$C_{10}$ optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

$R^2$ is a

group;

$R_b$ is a H, OH, $C_1$-$C_{10}$, optionally substituted alkyl or alkenyl group, an optionally substituted O—($C_1$-$C_7$ alkyl group) or O-aryl group, an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

with the proviso that at least one of $R^1$ and $R^2$ contains an $R_a$ or $R_b$ group which is an amine group which is substituted with at least one $C_1$-$C_{10}$ alkyl group which is substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group;

or a stereoisomer, pharmaceutically acceptable salt or solvate thereof.

2. The compound according to claim 1 wherein $R_a$ is OH or an optionally substituted O—($C_1$-$C_7$ alkyl group) or O-aryl group; and $R_b$ is an amine group which is optionally substituted with at least one $C_1$-$C_{10}$ alkyl group which may be optionally substituted, or an optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group.

3. The compound according to claim 1 wherein $R_a$ is OH.

4. The compound according to claim 1 wherein $R_a$ is an optionally substituted O—($C_1$-$C_7$ alkyl group) or O-aryl group.

5. The compound according to claim 2 wherein $R_a$ is an optionally substituted O—($C_1$-$C_7$ alkyl group) or O-aryl group.

6. The compound according to claim 2 wherein $R_a$ is an optionally substituted O—($C_1$-$C_7$ alkyl group).

7. The compound according to claim 1 wherein $R_b$ is an amine group which is optionally substituted with at least one $C_1$-$C_{10}$ alkyl group which may be optionally substituted, or a single optionally substituted aryl group, biphenyl group, ($C_1$-$C_6$) alkylenearyl group, ($C_1$-$C_6$) alkylenebiphenyl group, heteroaryl group, heterocyclic group, ($C_1$-$C_6$) alkylene heteroaryl group or ($C_1$-$C_6$) alkylene heterocyclic group.

8. The compound according to claim 2 wherein $R_b$ is an amine group which is optionally substituted with at least one $C_1$-$C_{10}$ alkyl group which may be optionally substituted, or a single optionally substituted aryl group, ($C_1$-$C_6$) alkylenearyl group, heteroaryl group, heterocyclic group, ($C_1$-$C_6$) alkylene heteroaryl group or ($C_1$-$C_6$) alkylene heterocyclic group.

9. The compound according to claim 4 wherein $R_b$ is an amine group which is optionally substituted with at least one $C_1$-$C_{10}$ alkyl group which may be optionally substituted, or a single optionally substituted aryl group, ($C_1$-$C_6$) alkylenearyl group, heteroaryl group, heterocyclic group, ($C_1$-$C_6$) alkylene heteroaryl group or ($C_1$-$C_6$) alkylene heterocyclic group.

10. The compound according to claim 1 wherein $R_a$ is an optionally substituted O—($C_1$-$C_7$ alkyl group) and $R_b$ is an amine group which is optionally substituted with at least one $C_1$-$C_{10}$ alkyl group which may be optionally substituted, or a single optionally substituted aryl group, ($C_1$-$C_6$) alkylenearyl group, heteroaryl group, heterocyclic group, ($C_1$-$C_6$) alkylene heteroaryl group or ($C_1$-$C_6$) alkylene heterocyclic group.

11. The compound according to claim 1 wherein $R_b$ is an amine group which is optionally substituted with a single cyclohexyl group, an optionally substituted phenyl group, or an optionally substituted benzyl group and $R_a$ is a O—($C_1$-$C_3$ alkyl) group or an O-phenyl group.

12. The compound according to claim 2 wherein $R_b$ is an amine group which is optionally substituted with a single cyclohexyl group, an optionally substituted phenyl group, or an optionally substituted benzyl group and $R_a$ is a O—($C_1$-$C_3$ alkyl) group or an O-phenyl group.

13. The compound according to claim 4 wherein $R_b$ is an amine group which is optionally substituted with a single cyclohexyl group, an optionally substituted phenyl group, or an optionally substituted benzyl group and $R_a$ is a O—($C_1$-$C_3$ alkyl) group or an O-phenyl group.

14. A pharmaceutical composition comprising an effective amount of a compound according to claim 1 in combination with a pharmaceutically acceptable carrier, additive or excipient.

15. A pharmaceutical composition comprising an effective amount of a compound according to claim 2 in combination with a pharmaceutically acceptable carrier, additive or excipient.

16. A pharmaceutical composition comprising an effective amount of a compound according to claim 3 in combination with a pharmaceutically acceptable carrier, additive or excipient.

17. A pharmaceutical composition comprising an effective amount of a compound according to claim 4 in combination with a pharmaceutically acceptable carrier, additive or excipient.

18. A pharmaceutical composition comprising an effective amount of a compound according to claim 5 in combination with a pharmaceutically acceptable carrier, additive or excipient.

19. A pharmaceutical composition comprising an effective amount of a compound according to claim 6 in combination with a pharmaceutically acceptable carrier, additive or excipient.

20. A pharmaceutical composition comprising an effective amount of a compound according to claim 7 in combination with a pharmaceutically acceptable carrier, additive or excipient.

21. A pharmaceutical composition comprising an effective amount of a compound according to claim 8 in combination with a pharmaceutically acceptable carrier, additive or excipient.

22. A pharmaceutical composition comprising an effective amount of a compound according to claim 9 in combination with a pharmaceutically acceptable carrier, additive or excipient.

23. A pharmaceutical composition comprising an effective amount of a compound according to claim 10 in combination with a pharmaceutically acceptable carrier, additive or excipient.

24. A pharmaceutical composition comprising an effective amount of a compound according to claim 11 in combination with a pharmaceutically acceptable carrier, additive or excipient.

25. A pharmaceutical composition comprising an effective amount of a compound according to claim 12 in combination with a pharmaceutically acceptable carrier, additive or excipient.

26. A pharmaceutical composition comprising an effective amount of a compound according to claim 13 in combination with a pharmaceutically acceptable carrier, additive or excipient.

27. A compound according to the chemical structure:

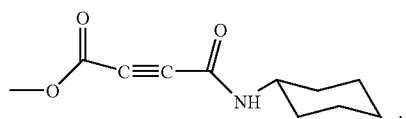

28. A pharmaceutical composition comprising an effective amount of a compound according to claim 27 in combination with a pharmaceutically acceptable carrier, additive or excipient.

* * * * *